United States Patent [19]

Hubbell et al.

[11] Patent Number: 5,529,914
[45] Date of Patent: Jun. 25, 1996

[54] GELS FOR ENCAPSULATION OF BIOLOGICAL MATERIALS

[75] Inventors: Jeffrey A. Hubbell, Concord, Mass.; Chandrashekhar P. Pathak, Austin, Tex.; Amarpreet S. Sawhney, Newton, Mass.; Neil P. Desai, Los Angeles, Calif.; Syed F. A. Hossainy, Austin, Tex.

[73] Assignee: The Board of Regents the Univeristy of Texas System, Austin, Tex.

[21] Appl. No.: 958,870

[22] Filed: Oct. 7, 1992

Related U.S. Application Data

[63] Continuation-in-part of Ser. No. 870,540, Apr. 20, 1992, Ser. No. 598,880, Oct. 15, 1990, abandoned, and Ser. No. 740,703, Aug. 5, 1991, Pat. No. 5,380,536, which is a division of Ser. No. 740,632, Aug. 5, 1991, Pat. No. 5,232,984, said Ser. No. 870,540, is a continuation-in-part of Ser. No. 843,485, Feb. 28, 1992, abandoned.

[51] Int. Cl.$^6$ .......................... C12N 11/04; C12N 11/02
[52] U.S. Cl. .......................... 435/182; 424/93.1; 424/487; 424/489; 424/493; 424/499; 427/213.3; 427/213.32; 427/213.35; 264/4; 264/4.1; 264/4.3; 435/177; 435/178; 522/87; 522/88; 522/89; 522/149; 522/151; 522/154; 522/181; 522/152
[58] Field of Search .......................... 427/213.35, 213.3, 427/213.32, 23.33; 264/43, 4.1, 4; 435/177, 178, 182; 424/93, 493, 499, 489, 487; 514/2; 522/87, 88, 89, 149, 151, 152, 154, 181

[56] References Cited

U.S. PATENT DOCUMENTS

| | | |
|---|---|---|
| 4,193,845 | 3/1980 | Kaetsu et al. . |
| 4,194,066 | 3/1980 | Kaetsu et al. . |
| 4,195,129 | 3/1980 | Fukui et al. . |
| 4,226,938 | 10/1980 | Yoshida et al. . |
| 4,272,617 | 6/1981 | Kaetsu et al. . |
| 4,283,325 | 8/1981 | Berthet et al. .......................... 424/630 |
| 4,298,002 | 11/1981 | Ronel et al. . |
| 4,321,117 | 3/1982 | Kaetsu et al. .......................... 522/5 |
| 4,329,332 | 5/1982 | Courvreur et al. .......................... 424/1.25 |
| 4,359,483 | 11/1982 | Kaetsu et al. .......................... 427/2 |
| 4,376,059 | 3/1983 | Davis et al. .......................... 424/499 |
| 4,411,754 | 10/1983 | Kaetsu et al. .......................... 522/73 |
| 4,511,478 | 4/1985 | Nowinski et al. . |
| 4,590,068 | 5/1986 | Berthet et al. . |
| 4,605,622 | 8/1986 | Hasegawa et al. . |
| 4,647,536 | 3/1987 | Mosbagh et al. .......................... 435/177 |
| 4,652,443 | 3/1987 | Yoshida et al. .......................... 424/487 |
| 4,729,904 | 3/1988 | Berthet et al. .......................... 424/487 |
| 4,774,178 | 9/1988 | Egerer et al. . |
| 4,822,535 | 4/1989 | Ekman et al. .......................... 264/4.3 |
| 4,889,722 | 12/1989 | Sheffield et al. . |
| 4,931,279 | 6/1990 | Bawa et al. .......................... 424/487 |
| 5,037,656 | 8/1991 | Pitt et al. . |
| 5,149,543 | 9/1992 | Cohen et al. .......................... 424/499 |
| 5,160,745 | 11/1992 | DeLuca et al. .......................... 424/499 |
| 5,183,690 | 2/1993 | Carr et al. .......................... 424/499 |
| 5,232,984 | 8/1993 | Hubbell et al. . |
| 5,268,182 | 12/1993 | Brinker et al. .......................... 424/499 |
| 5,271,961 | 12/1993 | Mathiowitz et al. .......................... 424/499 |
| 5,286,495 | 2/1994 | Batich et al. .......................... 424/499 |
| 5,288,500 | 2/1994 | Ibsen .......................... 424/499 |
| 5,334,640 | 8/1994 | Desai et al. . |
| 5,410,016 | 4/1995 | Hubbell et al. . |

FOREIGN PATENT DOCUMENTS

| | | |
|---|---|---|
| 0038172 | 10/1981 | European Pat. Off. .......................... 424/499 |
| 61-32271 | 2/1986 | Japan . |
| 62-14781 | 1/1987 | Japan . |
| 3184555 | 12/1989 | Japan . |
| 9110425 | 1/1991 | WIPO . |
| WO93/09176 | 5/1993 | WIPO . |
| WO93/18649 | 9/1993 | WIPO . |
| WO93/17669 | 9/1993 | WIPO . |
| WO93/21266 | 10/1993 | WIPO . |
| WO93/24112 | 12/1993 | WIPO . |
| WO93/24476 | 12/1993 | WIPO . |
| WO94/12161 | 6/1994 | WIPO . |
| WO94/15589 | 7/1994 | WIPO . |

OTHER PUBLICATIONS

Biotech Abs 87–05639 Abs. J62014781 (Jan. 1987) Taiyo Chem.

Crooks et al., "Microencapsulation of Mammalian Cells in a HEMA–MMA Copolymer: Effects on Capsule Morphology and Permeability," *Journal of Biomedical Materials Research*, 24:1241–1262 (1990).

Dupuy et al., "In Situ Polymerization of a Microencapsulating Medium Round Living Cells," *Jour. of Biomedical Materials Research*, 22:1061–1070 (1988).

Dupuy et al., "Microencapsulation of Isolated Pituitary Cells by Polyacrylamide Microlatex Coagulation on Agarose Beads," *Biomaterials*, 12:493–496 (1991).

Sefton et al., "Hydrophilic Polyacrylates for the Microencapsulation of Fibroblasts or Pancreatic Islets," *Journal of Controlled Release*, 6:177–187 (1987).

(List continued on next page.)

*Primary Examiner*—Herbert J. Lilling
*Attorney, Agent, or Firm*—Lyon & Lyon

[57] ABSTRACT

This invention provides novel methods for the formation of biocompatible membranes around biological materials using photopolymerization of water soluble molecules. The membranes can be used as a covering to encapsulate biological materials or biomedical devices, as a "glue" to cause more than one biological substance to adhere together, or as carriers for biologically active species. Several methods for forming these membranes are provided. Each of these methods utilizes a polymerization system containing water-soluble macromers, species which are at once polymers and macromolecules capable of further polymerization. The macromers are polymerized using a photoinitiator (such as a dye), optionally a cocatalyst, optionally an accelerator, and radiation in the form of visible or long wavelength UV light. The reaction occurs either by suspension polymerization or by interfacial polymerization. The polymer membrane can be formed directly on the surface of the biological material, or it can be formed on material which is already encapsulated.

69 Claims, 12 Drawing Sheets

OTHER PUBLICATIONS

Stevenson et al., "Microencapsulation of Mammalian Cells in a Hydroxyethyl Methacrylate–Methyl Methacrylate Copolymer: Preliminary Development," *Biomat. Art. Cells*, 16:747–769 (1988).

Tanaka et al., "Immobilization of Yeast Microbodies by Inclusion with Photo–crosslinkable Resins," *Eur. J. Biochem.*, 80:197–197 (1977).

Wen et al., "Microcapsules through Polymer Complexation," *Dept. of Chemistry and Inst. for Aviation Research* (1990).

Yung Yun Chun et al., "Studies of Microbial Transformation XIX. Use of Immobilized Cells of Streptomyces Roseochromogenes for the 160C–Hydroxylation of Dehydroepiandrosterone," *J. Gen. Appl. Microbiol.*, 27:505–509 (1981).

Desai et al., "Surface Modifications of Polymeric Biomaterials for Reduced Thrombogenicity," Polymeric Materials Science and Engineering, Proceedings of the ACS Division of Polymeric Materials Science and Engineering. 62:731–735 (1990).

Eaton, "Dye Sensitized Photopolymerization," *Advances in Photochemistry*, vol. 13, p. 427, John Wiley and Sons, Inc. (1986).

Fouassier et al., "Polymerisation induite sous irradiation laser visible 4, Le systeme eosine/photoamorceur ultra–violet/amine," *Makromol. Chem.* 192, 245–260 (1991).

Itoh et al., "Development of Novel Photocurable Medical–Use Resins; Molecular Design Considerations and Basic Properties," *Jap. J. Artif. Organs*, 18(1):132–136 (1989).

Karel et al., "The Immobilization of Whole Cells: Engineering Principles," *Chemical Engineering Science*, 20(5):1321–1354 (1985).

Karu, "Yearly Review—Effects of Visible Radiation on Cultured Cells," *Photochemistry and Photobiology*, 52(6):1089–1098 (1990).

Neckers et al., "Photopolymerization Using Derivatives of Fluorescein," American Chemical Society, Proceedings of the ACS Division of Polymeric Materials: Science and Engineering, vol. 60 (1989).

Sawhney et al., "Poly(ethylene oxide)–graft–poly(L–lysine) copolymers to enhance the biocompatibility of poly(L–lysine)–alginate microcapsule membranes," *Biomaterials*, 13(12):863–870 (1992).

Fukui et al., "Application of Biocatalysts Immobilized by Prepolymer Methods," *Adv. in Biochemical Eng. and Biotech.*, 29:1–33 (1984).

Fukui et al., "Application of Photo–Crosslinkable Resin to Immobilization of an Enzyme," *North–Holland Publishing Company—Amsterdam*, 66:179–182 (1976).

Fukui et al., "Entrapment of Biocatalysts with Photo–Cross–Linkable Resin Prepolymers and Urethane Resin Prepolymers," *Methods in Enzymology*, 135:230–253 (1987).

Fukui et al., "Several Novel Methods for Immobilization of Enzymes, Microbial Cells and Organelles," *Biochimie*, 62:381–386 (1980).

Gharapetian et al., "Encapsulation of Viable Cells Within Polyacrylate Membranes," *Biotechnology and Bioengineering*, 28:1595–1600 (1986).

Gharapetian et al., "Polyacrylate Microcapsules for Cell Encapsulation: Effects of Copolymer Structure on Membrane Properties," *Biotechnology and Bioengineering*, 30:775–779 (1987).

Gin et al., "Agarose Encapsulation of Islets of Langerhans: Reduced Toxicity in Vitro," *J. Microencapsulation*, 4:239–242 (1987).

Gombotz et al., "Immobilization of Poly(ethylene Oxide) on Poly(ethylene Terephthalate) Using a Plasma Polymerization Process," *Journal of Applied Polymer Science*, 37:91–107 (1989).

Hattori et al., "Fibroblast Cell Proliferation on Charged Hydroxyethyl Methacrylate Copolymers," *Journal of Colloid and Interface Science*, 104:72–78 (1985).

Hubbell et al., "Solution Technique to Incorporate Polyethylene Oxide and Other Water–Soluble Polymers into Surfaces of Polymeric Biomaterials," *Biomaterials*, 12:144–153 (1991).

Hubbell et al., "Surface Physical Interpenetrating Networks of Poly(ethylene terephthalate) and Poly(ethylene oxide) with Biomedical Applications," *Macromolecules*, 25:226–232 (1992).

Iwata et al., "Evaluation of Microencapsulated Islets in Agarose Gel as Bioartificial Pancreas by Studies of Hormone Secretion in Culture and by Xenotransplantation," *Diabetes*, 38:224–225 (1989).

Kimura et al., "Some Properties of an Immobilized Glycosys System of Yeast in Fermentative Phosphorylation of Nucleotides," *European J. Annl. Microbiol. Biotechnol.*, 11:78–80 (1981).

Lacy et al., "Maintenance of Normoglycemia in Diabetic Mice by Subcutaneous Xenografts of Encapsulated Islets," *Science*, 254:1782–1794 (1991).

Lamberti et al., "Microencapsulation of Mammalian Cells in Polyacrylates," *Applied Biochemistry and Biotechnology*, 10:101–103 (1984).

Mallabone et al., "Microencapsulation of Human Diploid Fibroblasts in Cationic Polyacrylates," *Dept. of Chem. Eng. and Applied Chem. and Centre for Biomaterials (1989)*.

Miyama et al., "Graft Copolymerization of Methoxypoly (ethylene Glycohol) Methacrylate onto Polyacrylonitrile and Evaluation of Nonthrombogenicity of the Copolymer," *Journal of Applied Polymer Science*, 35:115–125 (1988).

Okada et al., "Application of Entrapped Growing Yeast Cells to Peptide Secretion System," *Appl. Microbiol. Biotechnol.*, 26:112–116 (1987).

Omata et al., "Immobilization of Microbial Cells and Enzymes with Hydrophobic Photo–Crosslinkable Resin Prepolymers," *European J. Appl. Microbiol.*, 6: 207–215 (1979).

Omata et al., "Transformation of Steroids by Gel–Entrapped *Nocardia rhodocrous* Cells in Organic Solvent," *Eur. J. Appl. Microbiol. Biotechnol.*, 8:143–155 (1979).

Ronel et al., "Macroporous Hydrogel Membranes for a Hybrid Artificial Pancreas. 1. Synthesis and Chamber Fabrication," *Journal of Biomedical Materials Research*, 17:855–864 (1983).

GELS FOR ENCAPSULATION OF BIOLOGICAL MATERIALS

This application is a continuation-in-part of U.S. application Ser. No. 07/870,540, filed on Apr. 20, 1992 now abandoned, which is a continuation-in-part of U.S. application Ser. No. 07/843,485, filed on Feb. 28, 1992, now abandoned. This application is also a continuation-in-part of U.S. application Ser. No. 07/598,880, filed Oct. 15, 1990 now abandoned, and U.S. application Ser. No. 07/740,703, filed Aug. 5, 1991 now U.S. Pat. No. 5,380,536, which in turn is a division of U.S. application Ser. No. 07/740,632 filed Aug. 3, 1993 now U.S. Pat. No. 5,232,984. All of the above-identified applications are incorporated herein by reference.

BACKGROUND

Microencapsulation technology holds promise in many areas of medicine. For example, some important applications are treatment of diabetes (Goosen, et al., 1985), production of biologically important chemicals (Omata, et al., 1979), evaluation of anti-human immunodeficiency virus drugs (McMahon, et al., 1990), encapsulation of hemoglobin for red blood cell substitutes, and controlled release of drugs. During encapsulation using prior methods, cells are often exposed to processing conditions which are potentially cytotoxic. These conditions include heat, organic solvents and non-physiological pH which can kill or functionally impair cells. Proteins are often exposed to conditions which are potentially denaturing and can result in loss of biological activity.

Further, even if cells survive processing conditions, the stringent requirements of encapsulating polymers for biocompatibility, chemical stability, immunoprotection and resistance to cellular overgrowth, restrict the applicability of prior art methods. For example, the encapsulating method based on ionic crosslinking of alginate (a polyanion) with polylysine or polyornithine (polycation) (Goosen, et al., 1987) offers relatively mild encapsulating conditions, but the long-term mechanical and chemical stability of such ionically crosslinked polymers remains doubtful. Moreover, these polymers when implanted in vivo, are susceptible to cellular overgrowth (McMahon, et al., 1990) which restricts the permeability of the microcapsule to nutrients, metabolites, and transport proteins from the surroundings. This has been seen to possibly lead to starvation and death of encapsulated islets of Langerhans cells (O'Shea and Sun, 1986).

Thus, there is a need for a relatively mild cell encapsulation method which offers control over properties of the encapsulating polymer. The membranes must be non-toxically produced in the presence of cells, with the qualities of being permselective, chemically stable, and very highly biocompatible. A similar need exists for the encapsulation of biological materials other than cells and tissues.

Biocompatibility

Synthetic or natural materials intended to come in contact with biological fluids or tissues are broadly classified as biomaterials. These biomaterials are considered biocompatible if they produce a minimal or no adverse response in the body. For many uses of biomaterials, it is desirable that the interaction between the physiological environment and the material be minimized. For these uses, the material is considered "biocompatible" if there is minimal cellular growth on its surface subsequent to implantation, minimal inflammatory reaction, and no evidence of anaphylaxis during use. Thus, the material should elicit neither a specific humoral or cellular immune response nor a nonspecific foreign body response.

Materials which are successful in preventing all of the above responses are relatively rare; biocompatibility is more a matter of degree rather than an absolute state. The first event occurring at the interface of any implant with surrounding biological fluids is protein adsorption (Andrade, et al., 1986). In the case of materials of natural origin, it is conceivable that specific antibodies for that material exist in the repertoire of the immune defense mechanism of the host. In this case a strong immune response can result. Most synthetic materials, however, do not elicit such a reaction. They can either activate the complement cascade or adsorb serum proteins which mediate cell adhesion, called cell adhesion molecules (CAMs) (Buck, et al., 1987). The CAM family includes proteins such as fibronectin, vitronectin, laminin, von Willebrand factor, and thrombospondin.

Proteins can adsorb on almost any type of material. They have positively and/or negatively charged regions, as well as hydrophilic and hydrophobic regions. They can thus interact with implanted material through any of these various regions, resulting in cellular proliferation at the implant surface. Complement fragments such as C3b can be immobilized on the implant surface and act as chemoattractants. They in turn can activate inflammatory cells such as macrophages and neutrophils and cause their adherence and activation on the implant. These cells attempt to degrade and digest the foreign material.

In the event that the implant is nondegradable and is too large to be ingested by large single activated macrophages, the inflammatory cells may undergo frustrated phagocytosis. Several such cells can combine to form foreign body giant cells. In this process, these cells release peroxides, hydrolytic enzymes, and chemoattractant and anaphylactic agents such as interleukins, which increase the severity of the reaction. They also induce the proliferation of fibroblasts on foreign surfaces.

Fibroblasts secrete a collagenous matrix which ultimately results in encasement of the entire implant in a fibrous envelope. Cell adhesion can also be mediated on a charged surface by the cell surface proteoglycans such as heparin sulfate and chondroitin sulfate (van Wachem, et al., 1987). In such a process, intermediary CAMs are not required and the cell surface can interact directly with the surface of the implant.

Enhancing Biocompatibility

Past approaches to enhancing biocompatibility of materials started with attempts at minimization of interfacial energy between the material and its aqueous surroundings. Similar interfacial tensions of the solid and liquid were expected to minimize the driving force for protein adsorption and this was expected to lead to reduced cell adhesion and thrombogenicity of the surface. For example, Amudeshwari et al. used collagen gels cross-linked in the presence of HEMA and MMA (Amudeshwari, et al., 1986). Desai and Hubbell showed a poly(HEMA)-MMA copolymer to be somewhat non-thrombogenic (Desai, N. P. and Hubbell, 1989).

Protein adsorption and desorption, however, is a dynamic phenomenon, as seen in the Vroman effect. This effect is the gradual displacement of one serum protein by another, through a well-defined series, until only virtually irreversibly adsorbed proteins are present on the surface. Affinity of protein in a partially dehydrated state for the polymer surface has been proposed as a determining factor for protein adsorption onto a surface (Baier, 1990). Enhancement of surface hydrophilicity has resulted in mixed success; increased hydrophilicity or hydrophobicity does not have a clear relation with biocompatibility (Coleman, et al., 1982; Hattori, et al., 1985). In some cases, surfaces with intermediate hydrophilicities demonstrate proportionately less protein adsorption. The minimization of protein adsorption may depend both upon hydrophilicity and the absence of change, as described further below, perhaps in addition to other factors.

Use of Gels in Biomaterials

Gels made of polymers which swell in water such as poly (HEMA), water-insoluble polyacrylates, and agarose, have been shown to be capable of encapsulating islet cells and other animal tissue (Iwata, et al., 1989; Lamberti, et al., 1984). However, these gels have undesirable mechanical properties. Agarose forms a weak gel, and the polyacrylates must be precipitated from organic solvents, thus increasing the potential for cytotoxicity. Dupuy et al. (1988) have reported the microencapsulation of islets by polymerization of acrylamide to form polyacrylamide gels. However, the polymerization process, if allowed to proceed rapidly to completion, generates local heat and requires the presence of toxic cross-linkers. This usually results in mechanically weak gels whose immunoprotective ability has not been established. Moreover, the presence of a low molecular weight monomer is required which itself is cytotoxic.

Microcapsules formed by the coacervation of alginate and poly(L-lysine) have been shown to be immunoprotective e.g., O'Shea et al., 1986. However, implantation for periods up to a week has resulted in severe fibrous overgrowth on these microcapsules (McMahon, et al. 1990; O'Shea, et al., 1986).

Use of PEO in Biomaterials

The use of poly(ethylene oxide) (PEO) to increase biocompatibility is well documented in the literature. The presence of grafted PEO on the surface of bovine serum albumin has been shown by Abuchowski et al. (1977) to reduce immunogenicity in a rabbit and to increase circulation times of exogenous proteins in animals. The biocompatibility of algin-poly(L-lysine) microcapsules has been significantly enhanced by incorporating a graft copolymer of PLL and PEO on the microcapsule surface (Sawhney, et al., in press)

The grafting of methoxy PEO onto polyacrylonitrile surfaces was seen by Miyama et al. (1988) to render the polyacrylonitrile surface relatively non-thrombogenic. Nagoaka et al. synthesized a graft copolymer of methacrylates with PEO and found the resulting polymer to be highly non-thrombogenic. Desai and Hubbell have immobilized PEO on poly(ethylene terepthalate) surfaces by forming a physical interpenetrating network (Desai et al., 1992); they have shown these surface to be highly resistant to thrombosis (Desai et al, 1991) and to both mammalian and bacterial cell growth (Desai, et al., submitted).

PEO is a unique polymer in terms of structure. The PEO chain is highly water soluble and highly flexible. Polymethylene glycol, on the other hand, undergoes rapid hydrolysis, while polypropylene oxide is insoluble in water. PEO chains have an extremely high motility in water and are completely non-ionic in structure. The synthesis and characterization of PEO derivatives which can be used for attachment of PEO to various surfaces, proteins, drugs etc. has been reviewed (Harris, 1985). Other polymers are also water soluble and non-ionic, such as poly(N-vinyl pyrrolidinone) and poly(ethyl oxazoline). These have been used to reduce interaction of cells with tissues. N. P. Desai et al. (1991). Water soluble ionic polymers, such as hyaluronic acid, have also been used to reduce cell adhesion to surfaces and can similarly be used.

Immobilization of PEO on a charged surface, such as a coacervated membrane of alginate-PLL, results in shielding of surface charges by the non-ionic PEO (Sawhney et al., in press). The highly motile PEO chain sweeps out a free volume in its microenvironment. The free volume exclusion effect makes the approach of a macromolecule (viz., a protein) close to a surface which has grafted PEO chains sterically unfavorable (Miyama, et al., 1988; Nagoaka, et al.; Desai, et al.; Sun, et al., 1987). Thus protein adsorption is minimized and cell adhesion is reduced, resulting in surfaces showing increased biocompatibility.

Immobilization of PEO on a surface has been largely carried out by the synthesis of graft copolymers having PEO side chains (Sawhney, et al.; Miyama, et al., 1988; Nagoaka, et 81.). This process involves the custom synthesis of monomers and polymers for each application. The use of graft copolymers, however, still does not guarantee that the surface "seen" by a macromolecule consists entirely of PEO.

Electron beam cross-linking has been used to synthesize PEO hydrogels, and these biomaterials have been reported to be non-thrombogenic (Sun, et al., 1987; Dennison, H. A., 1986). However, use of an electron beam precludes the presence of any living tissue due to the sterilizing effect of this radiation. Also, the networks produced are difficult to characterize due to he non-specific cross-linking induced by the electron beam.

Photopolymerizable PEG diacrylates have been used to entrap yeast cells for fermentation and chemical conversion (Kimura et al. 1981; Omata et al., 1981; Okada et al. 1987). However, yeast cells are widely known to be much hardier, resistant to adverse environments and elevated temperatures, and more difficult to kill when compared to mammalian cells and human tissues. For example, yeast may be grown anaerobically, whereas mammalian cells may not; yeast are more resistant to organic solvents (e.g., ethanol to 12%) than are mammalian cells (e.g., ethanol to <1%); and yeast possess a polysaccharide cell wall, whereas mammalian cells, proteins, polysaccharides, and drugs do not. None of these references, however, discuss the exposure of sensitive eukaryotic tissue, organisms, or sensitive molecules to the chemical conditions used during polymerization because their polymerization conditions are incompatible with sensitive materials. For example, there are no reports of the encapsulation of mammalian cells using prior art photosensitive prepolymers without a marked loss of cellular function.

Other earlier encapsulations of cells within photopolymerizable materials have focused on microbial cells (Kimura et al., 1981; Omata et al., 1981; Okada et al., 1987; Tanaka et al., 1977; Omata et al 1979a; Omata et al., 1979b; Chun et al. 1981; Fukui et al., 1976; Fukui et al., 1984). Each of these reports, however, describes the use of near ultraviolet light (wavelength<320 nm), which is injurious to more sensitive cells such as mammalian cells or higher eukaryotic cells. In the original presentation of the technique (Fukui et al., 1976), the authors state in the final sentence that the technique would be appropriate for microbial cells, but provide no indication of usefulness for more sensitive cells. In a more recent and complete review of the technique (Fukui et al., 1984), the authors, in section 6 entitled "Entrapped Living Cells" provide no teaching regarding cells other than microbial cells, and in section 7 entitled "Future Prospects" they also provide no such teaching.

Moreover, the prior use of such materials for the entrapment of biological materials is entirely focused on industrial technology, rather than biomedical technology. For example, no attention is paid to biocompatibility, including formulation of the gel to avoid the problems described above. This is an important issue, since bioincompatibility in biomedical applications leads to xenograft failure in therapeutically transplanted cells for the evaluation of drug efficacy (O'Shea et al., 1986) and to xenograft failure in diagnostically transplanted cells (McMahon et al., 1990). Similarly, bioincompatibility would lead to the failure of encapsulated enzymes (for example, therapeutic enzymes encapsulated and circulating or implanted in a blood-rich tissue). Such encapsulated and entrapped enzymes could leave the circulation by interaction with the reticuloendothelial system (Hunt et al., 1985) or could become overgrown with tissues in a foreign body reaction.

Other ways of producing PEO hydrogels include use of PEO chains end capped with n-alkane chains, which associate in aqueous media to form stable gels (Knowles, et al., 1990). No biological properties of these materials have been reported, however. Thus, the prior art contains no description of methods to form biocompatible PEO networks on three-dimensional living tissue surfaces without damaging encapsulated tissue.

Among the techniques for encapsulating mammalian tissue with polymers other than PEO is a method of photopolymerizing the monomer 2-hydroxyethyl methacrylate ("HEMA") and the crosslinking agent ethylene glycol dimethacrylate ("EGDA") in a cylindrical mold containing the biological material (Ronel, et al., 1981). The product of this reaction, a cylindrical gel with cells embedded throughout, is frozen and then finely ground into small particles. This technique, however, suffers from a number of disadvantages. First, because the cylindrical gel is broken along random planes, shearing will often occur through pockets of cells, leaving some cells exposed to the host immune system. Second, HEMA and EGDA are small cytotoxic molecules capable of penetrating the cellular membrane. Third, the resulting polymer membrane has uneven pore sizes which vary to an upper limit of 20 microns, thereby allowing transit of immune response molecules. These drawbacks are reflected in data which show that tissue remains viable for only 2–3 days after this encapsulation process.

SUMMARY OF THE INVENTION

This invention provides novel methods for the formation of biocompatible membranes around biological materials using photopolymerization of water soluble molecules. The membranes can be used as a covering to encapsulate biological materials or biomedical devices, as a "glue" to cause more than one biological substance to adhere together, or as carriers for biologically active species.

Several methods for forming these membranes are provided. Each of these methods utilizes a polymerization system containing water-soluble macromers, species which are at once polymers and macromolecules capable of further polymerization. The macromers are polymerized using a photoinitiator (such as a dye), optionally a cocatalyst, optionally an accelerator, and radiation in the form of visible or long wavelength UV light. The reaction occurs either by suspension polymerization or by interfacial polymerization. The polymer membrane can be formed directly on the surface of the biological material, or it can be formed on material which is already encapsulated.

Ultrathin membranes can be formed by the methods described herein. These ultrathin membranes allow for optimal diffusion of nutrient and bioregulator molecules across the membrane, and great flexibility in the shape of the membrane. Such thin membranes produce encapsulated material with optimal economy of volume. Biological material thus coated can be packed into a relatively small space without interference from bulky membranes.

The thickness and pore size of membranes formed can be varied. This variability allows for "perm-selectivity"—membranes can be adjusted to the desired degree of porosity, allowing only preferred molecules to permeate the membrane, while acting as a barrier against larger undesired molecules. Thus, the membranes are immunoprotective in that they prevent the transfer of antibodies or cells of the immune system.

When the encapsulated biological material is cellular in nature, the absence of small monomers in the polymerization solution prevents the diffusion of toxic molecules into the cell. In this manner the present invention provides a polymerization system which is more biocompatible than any available in the prior art.

Additionally, the polymerization method utilizes short bursts of visible or long wavelength UV light which is nontoxic to biological material. Bioincompatible polymerization initiators employed in the prior art are also eliminated.

According to the present invention, membrane formation occurs under physiological conditions. Thus, no damage is done to the enclosed biological material due to harsh pH, temperature, or ionic conditions.

Because the membrane adheres to the biological material, the membrane can be used as an adhesive to fasten more than one biological substance together. The macromers are polymerized in the presence of these substances which are in close proximity. The membrane forms in the interstices, effectively gluing the substances together.

Additionally, utilizing the tendency of the membrane to adhere to biological material, a membrane can be formed around or on a biologically active substance to act as a carrier for that substance.

DETAILED DESCRIPTION

Figure 1:
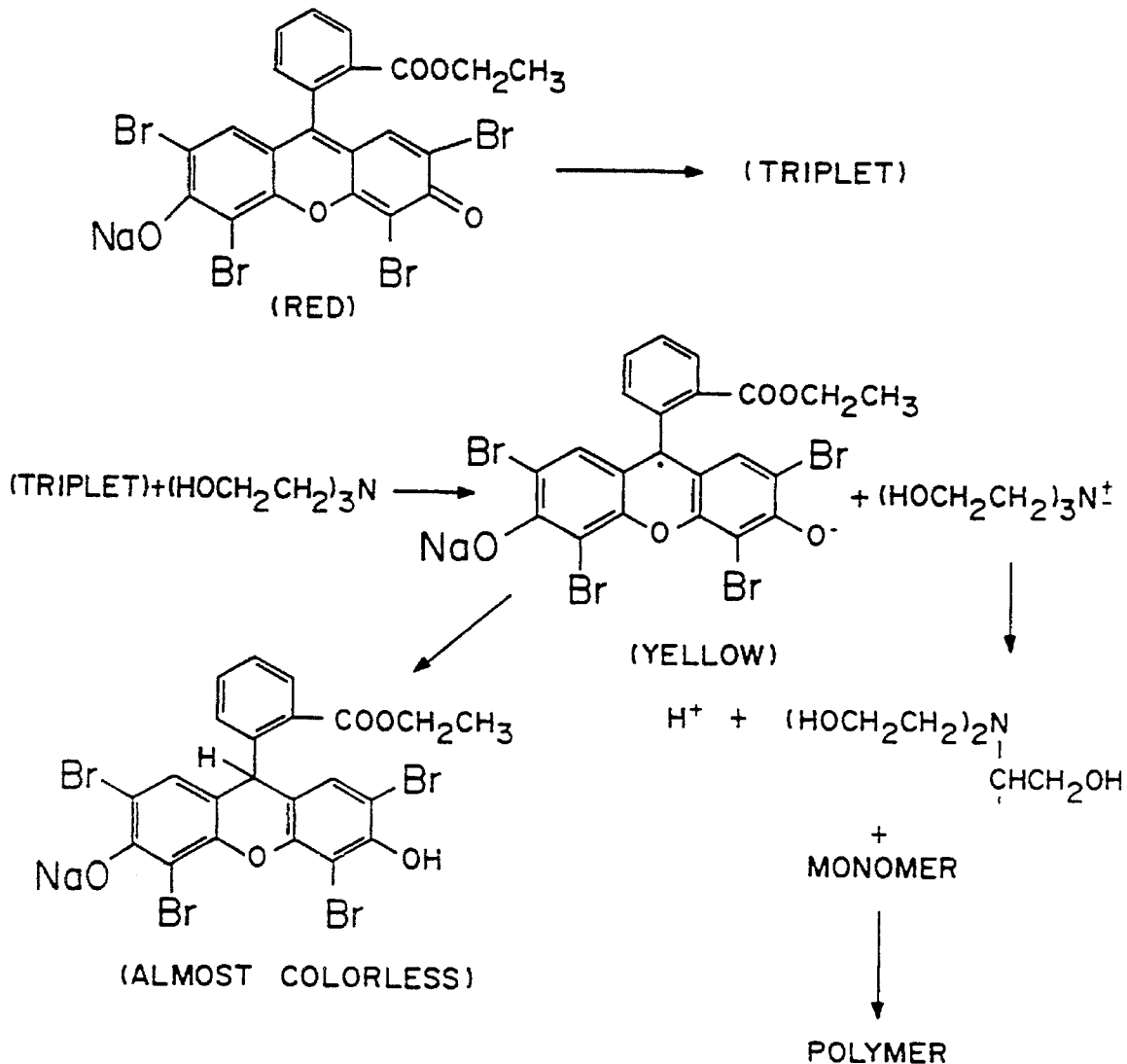
FIG. 1 is diagrammatic representation of photoinitiation with xanthine dyes, ethyl eosin shown here.

By a variety of methods, this invention provides a means for creating biocompatible membranes of varying thickness on the surface of a variety of biological materials. The polymerization occurs by a free-radical reaction, causing a "macromer" with at least two ethylenically unsaturated moieties to form a crosslinked polymer. The components of this reaction are:

(1) a photoinitiator, preferably eosin dye;

(2) a "macromer," preferably polyethylene glycol (PEG) diacrylate, m.w. 18.5 kD. This component is at once a polymer and a macromolecule capable of further polymerization;

(3) optionally a cocatalyst, preferably triethanolamine; and (4) optionally, an accelerator.

These components are mixed in varying combinations, and the mixture is exposed to longwave UV or visible light ("radiation"), preferably of wavelength 350–700 nm, most preferred at 365–514 nm, to initiate polymerization. A network is formed as the macromers polymerize in a variety of directions.

Four methods are used to effect polymerization to form biocompatible membranes. These are referred to below as the "bulk suspension polymerization" method, the "microcapsule suspension polymerization" method, the "microcapsule interfacial polymerization" method, and the "direct interfacial polymerization" method. They utilize either suspension or interfacial polymerization techniques on either coated or uncoated biological material.

Bulk Suspension Polymerization Method

In this embodiment of the invention the core biological material is mixed in an aqueous macromer solution (composed of the macromer, cocatalyst and optionally an accelerator) with the photoinitiator. Small globular geometric structures such as spheres, ovoids, or oblongs are formed, preferably either by coextrusion of the aqueous solution with air or with a non-miscible substance such as oil, preferably mineral oil, or by agitation of the aqueous phase in contact with a non-miscible phase such as an oil phase to form small droplets. The macromer in the globules is then polymerized when exposed to radiation. Because the macromer and initiator are confined to the globules, the structure resulting from polymerization is a capsule in which the biological material is enclosed. This is a "suspension polymerization" whereby the entire aqueous portion of the globule polymerizes to form a thick membrane around the cellular material.

Microcapsule Suspension Polymerization Method

This embodiment of the invention employs microencapsulated material as a core about which the macromer is polymerized in a suspension polymerization reaction. The biological material is first encapsulated, such as in an alginate microcapsules. The microcapsule is then mixed as in the first embodiment with the macromer solution and the photoinitiator, and then polymerized by radiation.

This method takes advantage of the extreme hydrophilicity of PEG macromer, and is especially suited for use with hydrogel microcapsules such as alginate-poly(L-lysine). The microsphere is swollen in water. When a macromer solution (with the initiating system) is forced to phase separate in a hydrophobic medium, such as mineral oil, the PEG macromer solution prefers to stay on the hydrophilic surface of the alginate microcapsule. When this suspension is irradiated, the PEG macromer undergoes polymerization and gelation, forming a thin layer of polymeric, water insoluble gel around the microsphere. Agarose beads have been used in an analogous way by Gin et al. (1987) as scaffolds to carry out polymerization of acrylamide. However, that method is limited by potential toxicity associated with the use of a low molecular weight monomer, as opposed to the macromer precursors of the present invention.

This technique preferably involves coextrusion of the microcapsule in a solution of macromer and photoinitiator, the solution being in contact with air or a liquid which is non-miscible with water, to form droplets which fall to a container such as a petri dish containing a solution such as mineral oil in which the droplets are not miscible. The non-miscible liquid is chosen for its ability to maintain droplet formation. Additionally, if the membrane-encapsulated material is to be injected or implanted in an animal, any residue should be non-toxic and non-immunogenic. Mineral oil is a preferred non-miscible liquid.

On the petri dish the droplets are exposed to radiation which causes polymerization. This coextrusion technique results in a crosslinked polymer coat of greater than 50 microns thickness. Alternatively, the microcapsules may be suspended in a solution of macromer and photoinitiator which is agitated in contact with a non-miscible phase such as an oil phase. The emulsion which results is irradiated to form a polymer coat, again of greater than 50 microns thickness.

Microcapsule Interfacial Polymerization Method

In this embodiment, the biological material is also microencapsulated as in the previous method. However, rather than suspension polymerization, interfacial polymerization is utilized to form the membrane. This involves coating the microcapsule with photoinitiator, suspending the microcapsule in the macromer solution, and immediately irradiating. By this technique a thin polymer coat, of less than 50 microns thickness, is formed about the microcapsule, because the photoinitiator is present only at the microcapsule surface and is given insufficient time to diffuse far into the macromer solution. As a result, the initiator is present in only a thin shell of the aqueous solution, causing a thin layer to be polymerized.

When the microcapsules are in contact with dye solution, the dye penetrates into the inner core of the microcapsule as well as adsorbing to the surface. When such a microcapsule is put into a solution containing a macromer and, optionally, a cocatalyst such as triethanolamine, and exposed to laser light, initially all the essential components of the reaction are present only at and just inside the interface of microcapsule and macromer solution. Hence, the polymerization and gelation (if multifunctional macromer is used) initially takes place only at the interface, just beneath it, and just beyond it. If left for longer periods of time, the dye starts diffusing from the inner core of the microsphere into the solution; similarly, macromers start diffusing inside the core.

Polymerization and subsequent gelation are very rapid (typical gelation times are 100 ms) (Fouassier, et al., 1985; Chesneau, et al., 1985). Because diffusion is a much slower process than polymerization, not the entire macromer solution is polymerized or gelled. Essentially the reaction is restricted to the near surface only. The dye, being a smaller molecule and being weakly bound to the capsule materials, keeps diffusing out of the microsphere. If this diffusion occurs under laser irradiation, then dye at the interface is used continuously to form a thicker gel layer. The thickness of the coating can thus be directed by controlling the reaction conditions.

Figure 2A:
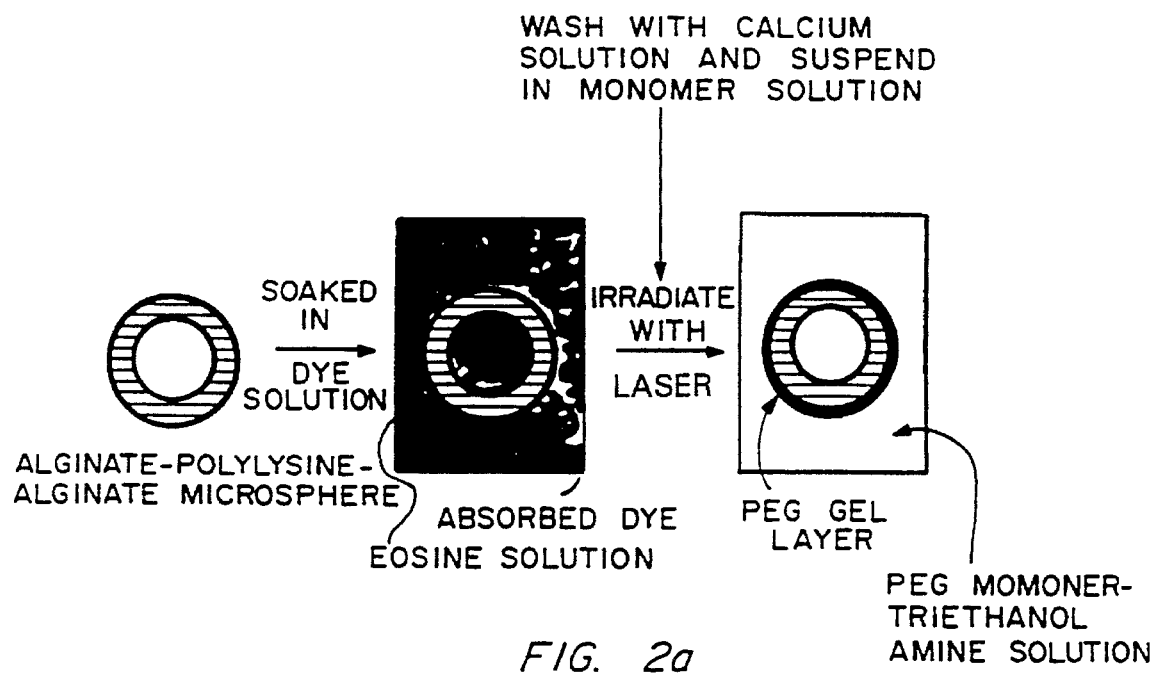
FIG. 2A is schematic representation of the process of dye diffusion under laser irradiation to form a gel layer at the interface by photopolymerization.
Figure 2B:
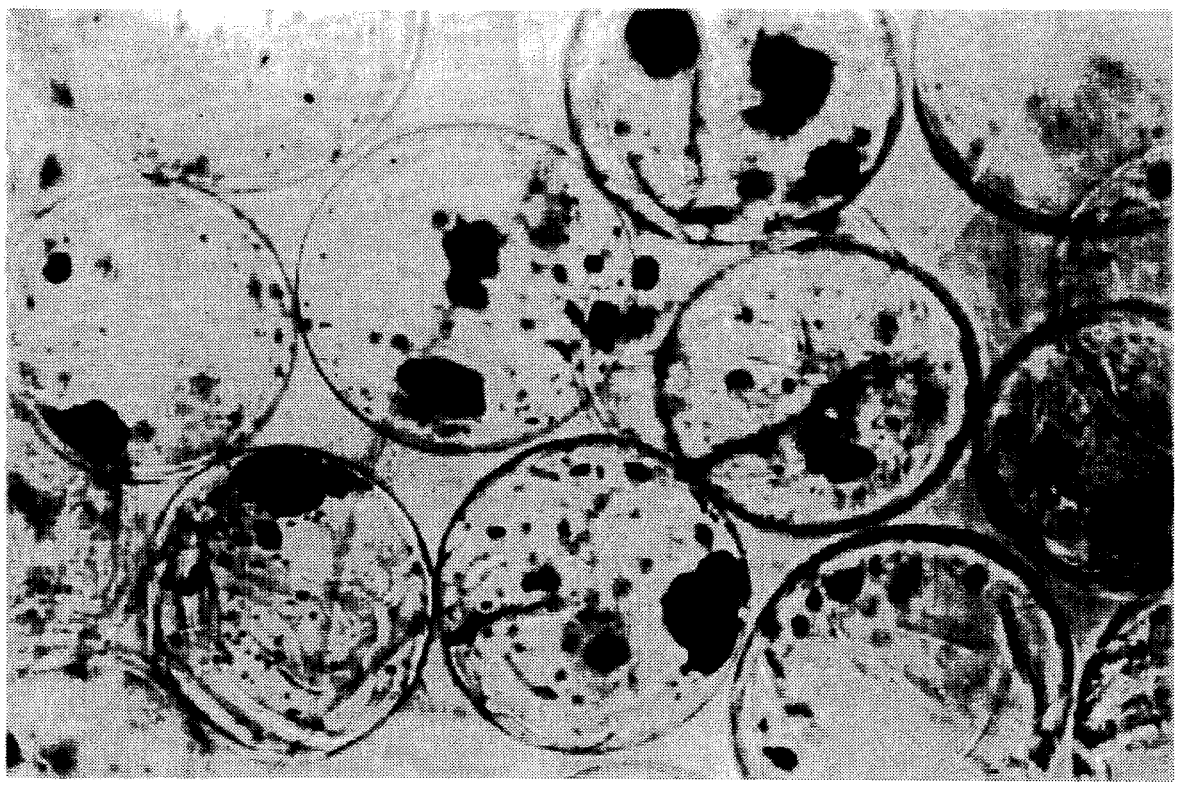
FIG. 2B is alginate/PLL microspheres containing islets coated by the technique depicted in FIG. 2A.

A schematic representation of this process is shown in FIG. 2A. The amount, thickness or size and rigidity of the gel formed will depend on the size and intensity of the beam, time of exposure, initiator, macromer molecular weight, and macromer concentration (see below). Alginate/PLL microspheres containing islets coated by this technique are shown in FIG. 2B.

Direct Interfacial Polymerization Method

The fourth embodiment of this invention utilizes interfacial polymerization to form a membrane directly on the surface of the biological material. This results in the smallest capsules and thus achieves optimal economy of volume. Tissue is directly coated with photoinitiator, emersed in the macromer solution, and immediately irradiated. This technique results in a thin polymer coat surrounding the tissue since there is no space taken up by a microcapsule, and the photoinitiator is again present only in a thin shell of the macromer solution.

Use as an Adhesive

It is usually difficult to get good adhesion between polymers of greatly different physicochemical properties. The concept of a surface physical interpenetrating network was presented by Desai and Hubbel (N. P. Desai et al. (1992)). This approach to incorporating into the surface of one polymer a complete coating of a polymer of considerably different properties involved swelling the surface of the polymer to be modified (base polymer) in a mutual solvent, or a swelling solvent, for the base polymer and for the polymer to be incorporated (penetrant polymer). The penetrant polymer diffused into the surface of the base polymer. This interface was stabilized by rapidly precipitating or deswelling the surface by placing the base polymer in a nonsolvent bath. This resulted in entanglement of the penetrant polymer within the matrix of the base polymer at its surface in a structure that was called a surface physical interpenetrating network.

This approach can be improved upon by photopolymerizing the penetrant polymer upon the surface of the base polymer in the swollen state. This results in much enhanced stability over that of the previous approach and in the enhancement of biological responses to these materials. The penetrant may be chemically modified to be a prepolymer (macromer), i.e. capable of being polymerized itself. This polymerization can be initiated thermally or by exposure to visible, ultraviolet, infrared, gamma ray, or electron beam irradiation, or to plasma conditions. In the case of the relatively nonspecific gamma ray or electron beam radiation reaction, chemical incorporation of particularly reactive sites may not be necessary.

Polyethylene glycol (PEG) is a particularly useful penetrant polymer for biomedical applications where the lack of cell adhesion is desired. The previous work had demonstrated an optimal performance at a molecular weight of 18,500 D without chemical crosslinking. PEG prepolymers can be readily formed by acrylation of the hydroxyl groups at its termini or elsewhere within the chain. These prepolymers can be readily polymerized by the above described radiation methods. Photoinititated polymerization of these prepolymers is particularly convenient and rapid. There are a variety of visible light initiated and ultraviolet light initiated reactions that are initiated by light absorption by specific photochemically reactive dyes, described elsewhere herein. This same approach can be used for biomedical purposes with other water-soluble polymers, such as poly(N-vinyl pyrrolidinone), poly(N-isopropyl acrylamide), poly(ethyl oxazoline) and many others.

Additionally, it is usually difficult to obtain adhesives for wet surfaces and tissues. Water soluble prepolymers, for example PEG diacrylates, can be used for this purpose. When a water soluble polymer is placed in aqueous solution upon a tissue, the polymer diffuses into the surface of the tissue, within the protein and polysaccharide matrix upon the tissue but not within the cells themselves. When the water soluble polymer is a prepolymer and a visible, ultraviolet or infrared photoinitiator is included, the polymer penetrant may be exposed to the appropriate light to gel the polymer. In this way, the polymer is crosslinked within and around the matrix of the tissue in what is called an interpenetrating network. If the prepolymer is placed in contact with two tissues and the prepolymer is illuminated, then these two tissues are adhered together by the intermediate polymer gel.

Biological Materials

Due to the biocompatibility of the materials and techniques involved, a wide variety of materials can be used in conjunction with the present invention. For encapsulation, the techniques can be used with mammalian tissue and/or cells, as well as sub-cellular organelles and other isolated sub-cellular components. The membranes can be crafted to meet the perm-selectivity needs of the biological material enclosed. Cells which are to be used to produce desired products such as proteins are optimally encapsulated by this invention.

Examples of cells which can be encapsulated are primary cultures as well as established cell lines, including transformed cells. These include but are not limited to pancreatic islet cells, human foreskin fibroblasts, Chinese hamster ovary cells, beta cell insulomas, lymphoblastic leukemia cells, mouse 3T3 fibroblasts, dopamine secreting ventral mesencephalon cells, neuroblastoid cells, adrenal medulla cells, and T-cells. As can be seen from this partial list, cells of all types, including dermal, neural, blood, organ, muscle, glandular, reproductive, and immune system cells can be encapsulated successfully by this method. Additionally, proteins (such as hemoglobin), polysaccharides, oligonucleotides, enzymes (such as adenosine deaminase), enzyme systems, bacteria, microbes, vitamins, cofactors, blood clotting factors, drugs (such as TPA, streptokinase or heparin), antigens for immunization, hormones, and retroviruses for gene therapy can be encapsulated by these techniques.

The biological material can be first enclosed in a structure such as a polysaccharide gel. (Lim, U.S. Pat. No. 4,352,883; Lim, U.S. Pat. No. 4,391909; Lim, U.S. Pat. No. 4,409,331; Tsang, et al., U.S. Pat. No. 4,663,286; Goosen et al., U.S.

Pat. No. 4,673,556; Goosen et al., U.S. Pat. No. 4,689,293; Goosen et al., U.S. Pat. No. 4,806,355; Rha et al., U.S. Pat. No. 4,744,933; Rha et al., U.S. Pat. No. 4,749,620, incorporated herein by reference.) Such gels can provide additional structural protection to the material, as well as a secondary level of perm-selectivity.

Macromers

Polymerization via this invention utilizes macromers rather than monomers as the building blocks. The macromers are small polymers which are susceptible to polymerization into the larger polymer membranes of this invention. Polymerization is enabled because the macromers contain carbon-carbon double bond moieties, such as acrylate, methacrylate, ethacrylate, 2-phenyl acrylate, 2-chloro acrylate, 2-bromo acrylate, itaconate, acrylamide, methacrylamide, and styrene groups. The macromers are water soluble compounds and are non-toxic to biological material before and after polymerization.

Examples of macromers are ethylenically unsaturated derivatives of poly(ethylene oxide) (PEO), poly(ethylene glycol) (PEG), poly(vinyl alcohol) (PVA), poly(vinylpyrrolidone) (PVP), Poly(ethyloxazoline) (PEOX), poly(amino acids), polysaccharides such as alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives and carrageenan, and proteins such as gelatin, collagen and albumin. An example of a macromer is

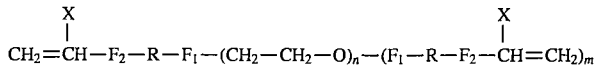

where $F_1$=CONH, COO or NHCOO

X=H, $CH_3$, $C_2H_5$, $C_6H_5$, Cl, Br, OH or $CH_2COOH$ $F_2$=COO, CONH, O or $C_6H_4$,

R=$CH_2$ or -alkyl-, n $\geq$5, and m $\geq$3.

These macromers can vary in molecular weight from 0.2–100 kD, depending on the use. The degree of polymerization, and the size of the starting macromers, directly affect the porosity of the resulting membrane. Thus, the size of the macromers are selected according to the permeability needs of the membrane. For purposes of encapsulating cells and tissue in a manner which prevents the passage of antibodies across the membrane but allows passage of nutrients essential for cellular metabolism, the preferred starting macromer size is in the range of 10 kD to 18.5 kD, with the most preferred being around 18.5 kD. Smaller macromers result in polymer membranes of a higher density with smaller pores.

Photoinitiating Dyes

The photoinitiating dyes capture light energy and initiate polymerization of the macromers. Any dye can be used which absorbs light having frequency between 320 nm and 900 nm, can form free radicals, is at least partially water soluble, and is non-toxic to the biological material at the concentration used for polymerization. Examples of suitable dyes are ethyl eosin, eosin Y, fluorescein, 2,2-dimethoxy,2-phenylacetophenone, 2-methoxy, 2-phenylacetophenone, camphorquinone, rose bengal, methylene blue, erythrosin, phloxime, thionine, riboflavin and methylene green. The preferred initiator dye is ethyl eosin due to its spectral properties in aqueous solution.

Cocatalyst

The cocatalyst is a nitrogen based compound capable of stimulating the free radical reaction. Primary, secondary, tertiary or quaternary amines are suitable cocatalysts, as are any nitrogen atom containing electron-rich molecules. Cocatalysts include, but are not limited to, triethanolamine, triethylamine, ethanolamine, N-methyl diethanolamine, N,N-dimethyl benzylamine, dibenzyl amine, N-benzyl ethanolamine, N-isopropyl benzylamine, tetramethyl ethylenediamine, potassium persulfate, tetramethyl ethylenediamine, lysine, ornithine, histidine and arginine.

Accelerator

The accelerator which is optionally included in the polymerization mixture is a small molecule containing an allyl, vinyl, or acrylate group, and is capable of speeding up the free radical reaction. Accelerators include, but are not limited to, N-vinyl pyrrolidinone, 2-vinyl pyridine, 1-vinyl imidazole, 9-vinyl carbazole, acrylic acid, and 2-allyl-2-methyl-1,3-cyclopentane dione, with N-vinyl pyrrolidinone being the preferred accelerator.

Radiation Wavelength

The radiation used to initiate the polymerization is either longwave UV or visible light, with a wavelength in the range of 320–900 nm. Preferably, light in the range of 350–700 nm, and even more preferred in the range of 365–514 nm, is used. This light can be provided by any appropriate source able to generate the desired radiation, such as a mercury lamp, longwave UV lamp, He—Ne laser, or an argon ion laser.

Thickness and Conformation of Polymer Layer

Membrane thickness affects a variety of parameters, including perm-selectivity, rigidity, and size of the membrane. In the interfacial polymerization method, the duration of the radiation can be varied to adjust the thickness of the polymer membrane formed. This correlation between membrane thickness and duration of irradiation occurs because the photoinitiator diffuses at a steady rate, with diffusion being a continuously occurring process. Thus, the longer the duration of irradiation, the more photoinitiator will initiate polymerization in the macromer mix, the more macromer will polymerize, and a thicker coat will be formed. Additional factors which affect membrane thickness are the number of reactive groups per macromer, the concentration of accelerators in the macromer solution. This technique allows the creation of very thin membranes because the photoinitiator is first present in a very thin layer at the surface of the biological material, and polymerization only occurs where the photoinitiator is present.

The suspension polymerization method forms a somewhat thicker membrane than the interfacial polymerization method. This is because polymerization occurs in the suspension method throughout the macromer mix. The thickness of membranes formed by the suspension method is determined in part by the viscosity of the macromer solution, the concentration of the macromer in that solution, the fluid mechanical environment of the suspension and surface active agents in the suspension. These membranes vary in thickness from 50–300 microns. The shape of the structure formed by suspension polymerization can be controlled by shaping the reaction mix prior to polymerization. Spheres can be formed by emulsion with a non-miscible liquid such as oil, coextrusion with such a liquid, or coextrusion with air. Cylinders may be formed by casting or extrusion, and slabs and discoidal shapes can be formed by casting. Additionally, the shape may be formed in relationship to an internal supporting structure such as a screening network of stable polymers (e.g. an alginate gel or a woven polymer fiber) or nontoxic metals.

The overall amount, thickness, and rigidity of the membrane formed depends on the interaction of several parameters, including the size and intensity of the radiation beam, duration of exposure of the solution to the radiation, reactivity of the initiator selected, macromer molecular weight, and macromer concentration.

The invention can be used for a variety of purposes, some of which are enumerated below, along with benefits which accrue from the use of the invention:

a. Microencapsulating cells: more biocompatible, stronger, more stable, better control of permselectivity, less toxic conditions
b. Macroencapsulating cells: more biocompatible, stronger, more stable, better control of permselectivity, less toxic conditions, easier to incorporate internal or external supporting structure
c. Microencapsulating or macroencapsulating other tissues, with the same benefits
d. Microencapsulating or macroencapsulating pharmaceuticals: more biocompatible, less damaging to the pharmaceutical
e. Coating devices: ease of application, more biocompatible
f. Coating microcapsules: more biocompatible, strengthens them, ease of coating
g. Coating macrocapsules, microcapsules, microspheres and macrospheres: more biocompatible, ease of coating
h. Coating tissues to alter adhesion of other tissues: ease of coating, less toxicity to the tissues, conformal coating versus nonconformal
i. Adhesive between two tissues: ease of adhesion, rapidity of forming adhesive bond, less toxicity to tissues The invention described herein is further exemplified in the following Examples. While these Examples provide a variety of combinations useful in performing the methods of the invention, they are illustrative only and are not to be viewed as limiting in any manner the scope of the invention.

Example 1—Synthesis of PEG 6 kD Diacrylate
Example 2—Synthesis of PEG 18.4 kD Tetraacrylate
Example 3—Coating of Islet-Containing Alginate-PLL Microspheres by Surface Dye Adsorption
Example 4—Coating Islet-Containing Alginate-PLL Microspheres by the Oil Suspension Method
Example 5—Encapsulation of Islets of Langerhans
Example 6—Microencapsulation of Animal Cells
Example 7—Coating of Animal Cell-Containing Alginate-PLL Microspheres and Individual Cells by Surface Dye Adsorption
Example 8—Coating Animal Cell Containing Alginate-PLL Microspheres by the Oil Suspension Method
Example 9—Coating of Individual Islets of Langerhans by Surface Dye Adsorption
Example 10—Biocompatibility of PEO on Microspheres
Example 11—Permeability of PEO Gels
Example 12—Treatment of Silicone Rubber
Example 13—Treatment of Polyurethane
Example 14—Treatment of Ultrafiltration Membranes
Example 15—Treatment of Textured Materials and Hydrogels
Example 16—Treatment of Dense Materials
Example 17—Rate of Polymerization
Example 18—PEO Gel Interactions
Example 19—Characterization and Mechanical Analysis of PEO Gels
Example 20—Water Content of PEO Gels
Example 21—Mechanical Stability of PEO Gels after Implantation
Example 22—Monitoring of Calcification of PEO Gels
Example 23—Encapsulation of Neurotransmitter-Releasing Cells
Example 24—Encapsulation of Hemoglobin for Synthetic Erythrocytes
Example 25—Entrapment of Enzymes for Correction of Metabolic Disorders and Chemotherapy
Example 26—Cellular Microencapsulation for Evaluation of Anti-Human Immunodeficiency Virus Drugs In Vivo
Example 27—Use of PEG Gels as Adhesive to Rejoin Severed Nerve
Example 28—Surgical Adhesive
Example 29—Modification of PVA Polymer
Example 30—Use of Alternative Photopolymerizable Moieties
Example 31—Use of Alternative Photoinitiator/Photosensitizer Systems
Example 32—Formation of Alginate-PLL-Alginate Microcapsules with Photopolymerizable Polycations

EXAMPLE 1

Synthesis of PEG 6 kD Diacrylate

PEG acrylates of molecular weights 400 Da and 1,000 Da are commercially available from Sartomer and Dajac Inc., respectively. PEG 6 kD (20 g) was dissolved in 200 mL dichloromethane in a 250 mL round bottom flask. The flask was cooled to 0° C. and 1.44 mL of triethyl amine and 1.3 mL of acryloyl chloride were added with constant stirring under a dry nitrogen atmosphere. The reaction mixture was then brought to room temperature and stirred for 12 hr under a nitrogen atmosphere. It was then filtered, and the filtrate was precipitated by adding to a large excess of hexane. The crude monomer was purified by dissolving in dichloromethane and precipitating in hexane. Yield 69%.

EXAMPLE 2

Synthesis of PEG 18.4 kD Tetraacrylate

A tetrafunctional water soluble PEG (30 g; m.w. 18.5 kD) having the following structure was purchased from Polysciences, Inc.:

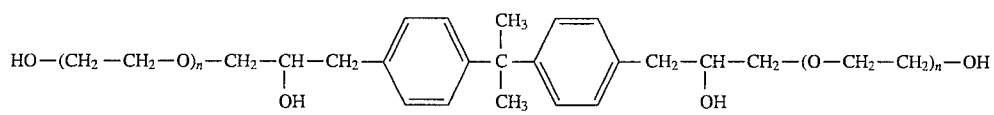

where $F_1$=CONH, COO or NHCOO

X=H, $CH_3$, $C_2H_5$, $C_6H_5$, Cl Br, OH or $CH_2COOH$ $F_2$=COO, CONH, O or $C_6H_4$, AND

R=$CH_2$ or -alkyl-.

The PEG was dried by dissolving in benzene and distilling off the water-benzene azeotrope. PEG 18.5 kD (59 g) was dissolved in 300 mL of benzene in a 500 mL flask. To this, 3.6 mL of triethylamine and 2.2 mL of acryloyl chloride were added under nitrogen atmosphere and the reaction mixture was refluxed for 2 hours. It was then cooled and stirred overnight. The triethyl amine hydrochloride was separated by filtration and the copolymer was recovered from filtrate by precipitating in a large excess of hexane. The polymer was further purified by dissolving in methylene chloride and reprecipitating in hexane. The polymer was dried at 50° C. under vacuum for 1 day. Yield 68%.

EXAMPLE 3

Coating of Islet-Containing Alginate-PLL

Microspheres by Surface Dye Adsorption

The microcapsule interfacial polymerization method was used to form membrane around alginate-PLL microcapsules containing islets. Alginate-PLL coacervated microspheres, containing one or two human pancreatic islets each, were suspended in a 1.1% $CaCl_2$ solution and aspirated free of excess solution to obtain a dense plug of microspheres. A solution of ethyl eosin (0.04% w/v) was prepared in a 1.1% $CaCl_2$ solution. This solution was filter-sterilized by passage through a 0.45 μm filter. The plug of microspheres was suspended in 10 mL of the eosin solution for 2 min to allow uptake of the dye. The microspheres were then washed four times with fresh 1.1% $CaCl_2$ to remove excess dye. A solution of PEG 18.5 tetraacrylate (2 mL; 23% w/v) containing 100 μL of a 3.5% w/v solution of triethanolamine in HEPES buffered saline was added to 0.5 mL of these microspheres. The microspheres were exposed to argon ion laser light for 30 seconds with periodic agitation. The suspension of microspheres was uniformly scanned with the light during this period. The microspheres were then washed with calcium solution and the process was repeated in order to further stabilize the coating.

A static glucose stimulation test (SGS) was performed on islets encapsulated in the microspheres coated with PEG gel. Data for insulin secretion in response to this challenge appears in Table 1. The islets were seen to be viable by dithizone staining. The SGS test data confirm the vitality and functionality of the islets.

TABLE 1

| | SGS | | |
|---|---|---|---|
| | Glucose Concentration (mg %) | | |
| | initial 60 | pulse 300 | subsequent 60 |
| | Insulin/Islet/hr (μU/mL)* | | |
| Diffusion Overcoat Method | 1.0 | 10.04 ± 3.56 | 2.5450.76 |
| Mineral Oil Overcoat Method | 1.0 | 10.23 ± 3.28 | 1.0250.78 |
| Free Islet Control | 1.0 | 3.74 ± 1.4 | 1.950.17 |

*Values are mean ± S.D., all are normalized as compared to the initial 60 mg %, after subjection to the 300 mg % glucose, the islets were resubjected to the initial dose.

PEG diacrylate macromers may be polymerized identically as the PEG tetraacrylate macromer described in this example.

EXAMPLE 4

Coating Islet-Containing Alginate-PLL
Microspheres by the Microcapsule Suspension
Polymerization Method This method takes advantage of the hydrophilic nature of PEG monomers. Alginate/PLL microspheres (2 mL), containing one or two human pancreatic islets each, were mixed with PEG tetraacrylate macromer solution (PEG mol wt 18.5 kD, 23% solution in saline) in a 50 mL transparent centrifuge tube. Triethanolamine (0.1M) and 0.5 mM ethyl eosin were mixed with macromer solution. The excess of macromer solution was decanted, 20 mL of mineral oil was added to the tube, and the reaction mixture was vortexed thoroughly for 5 minutes. Silicone oil will perform equally well in this synthesis but may have poorer adjuvant characteristics if there is any carry-over. Any other water-immiscible liquid may be used as the "oil" phase. Acceptable triethanolamine concentrations range from about 1 mM to about 100mM. Acceptable ethyl eosin concentrations range from about 0.01 mM to more than 10 mM.

The beads were slightly red due to the thin coating of macromer/dye solution, and they were irradiated for 20–50 sec with an argon ion laser (power 50–500 mW). Bleaching of the (red) ethyl eosin color suggested completion of the reaction. The beads were then separated from mineral oil and washed several times with saline solution. The entire procedure was carried out under sterile conditions.

Figure 3:
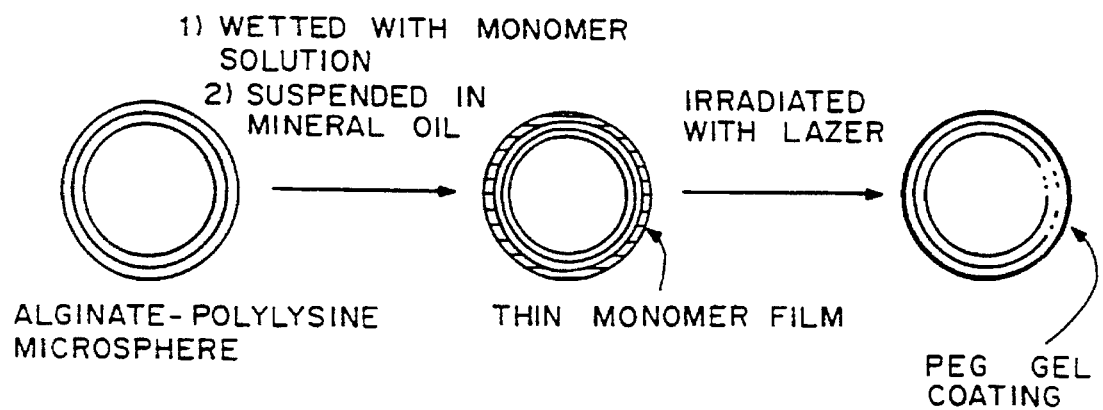
FIG. 3 is a schematic representation of the microsphere coating process in oil.

A schematic representation of the microsphere coating process in oil is shown in FIG. 3. Alginate/polylysine capsules are soluble in sodium citrate at pH 12. When these coated microspheres came in contact with sodium citrate at pH 12, the inner alginate/polylysine coacervate dissolves and a PEG polymeric membrane could still be seen (crosslinked PEG gels are substantially insoluble in all solvents including water and sodium citrate at pH 12). The uncoated control microspheres dissolved completely and rapidly in the same solution.

A static glucose challenge was performed on the islets as in Example 3. Data again appear in Table 1. The islets were seen to be viable and functional.

EXAMPLE 5

Encapsulation of Islets of Langerhans

This example makes use of the direct interfacial polymerization. Islets of Langerhans isolated from a human pancreas were encapsulated in PEG tetraacrylate macromer gels. 500 islets suspended in RPMI 1640 medium containing 10% fetal bovine serum were pelleted by centrifuging at 100 g for 3 min. The pellet was resuspended in 1 mL of a 23% w/v solution of PEO 18.5 kD diacrylate macromer in HEPES buffered saline. An ethyl eosin solution (5 μL) in vinyl pyrrolidone (at a concentration of 0.5%) was added to this solution along with 100 μL of a 5M solution of triethanolamine in saline. Mineral oil (20 mL) was then added to the tube which was vigorously agitated to form a dispersion of droplets 200–500 μm in size. This dispersion was then exposed to an argon ion laser with a power of 250 mW, emitting at 514 nm, for 30 sec. The mineral oil was then separated by allowing the microspheres to settle, and the resulting microspheres were washed twice with PBS, once with hexane and finally thrice with media.

Figure 4:
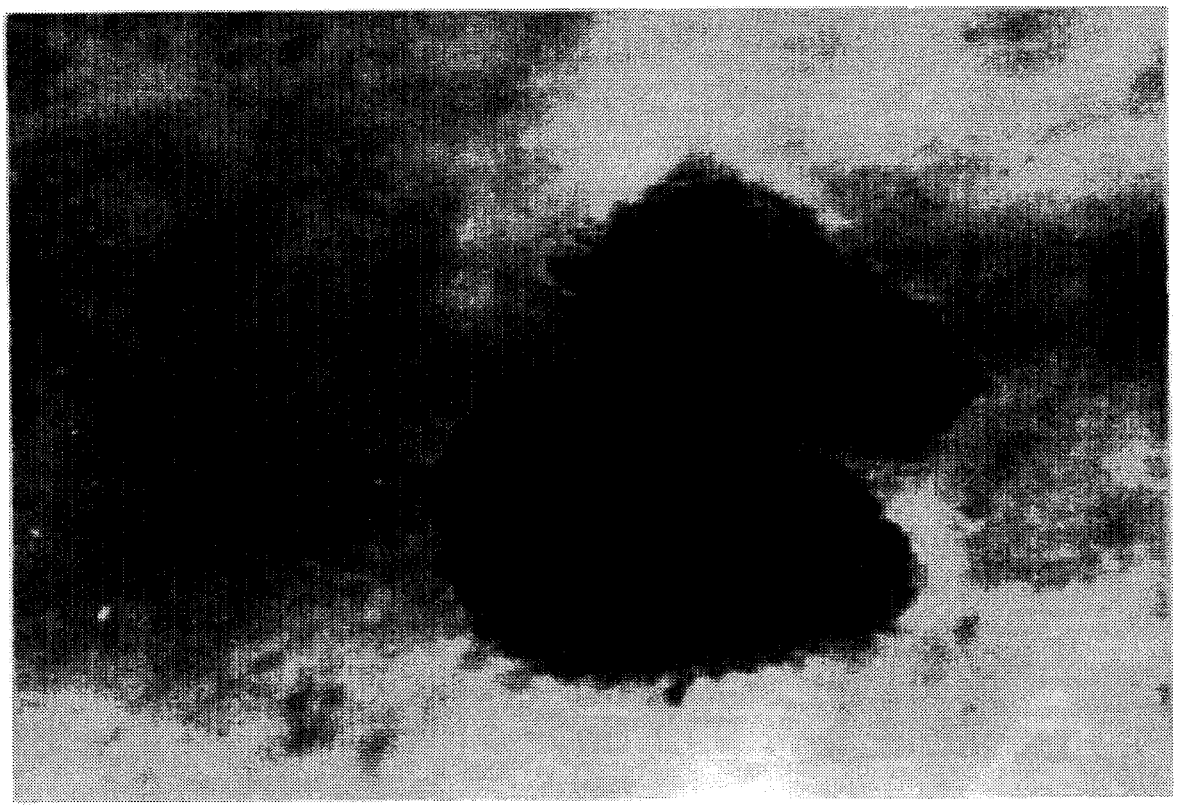
FIG. 4 shows islets of Langerhans encapsulated in a PEO gel.

FIG. 4 shows islets of Langerhans encapsulated in a PEO gel. The viability of the islets was verified by an acridine orange and propidium iodide staining method and also by dithizone staining. In order to test functional normalcy, an SGS test was performed on these islets. The response of the encapsulated islets was compared to that of free islets maintained in culture for the same time period. All islets were maintained in culture for a week before the SGS was performed. The results are summarized in Table 2. It can be seen that the encapsulated islets secreted significantly ($p<0.05$) higher insulin than the free islets. The PEO gel encapsulation process did not impair function of the islets and in fact helped them maintain their function in culture better than if they had not been encapsulated.

TABLE 2

| | Islet Insulin secretion | | |
|---|---|---|---|
| | Glucose Concentration (ma %) | | |
| | 60 | 300 | 60 |
| | uz,13/32 Insulin/Islet/hr | | ($\mu$U/mL)* |
| Free islets | 1.0 | 3.74+/−1.40 | 1.9+/−0.17 |
| Encapsulated Islets | 1.0 | 20.81+/−9.36 | 2.0+/−0.76 |

*Values are mean +/− S.D., normalized to initial basal level at 60 mg % glucose.

EXAMPLE 6

Microencapsulation of Animal Cells

Figure 5:
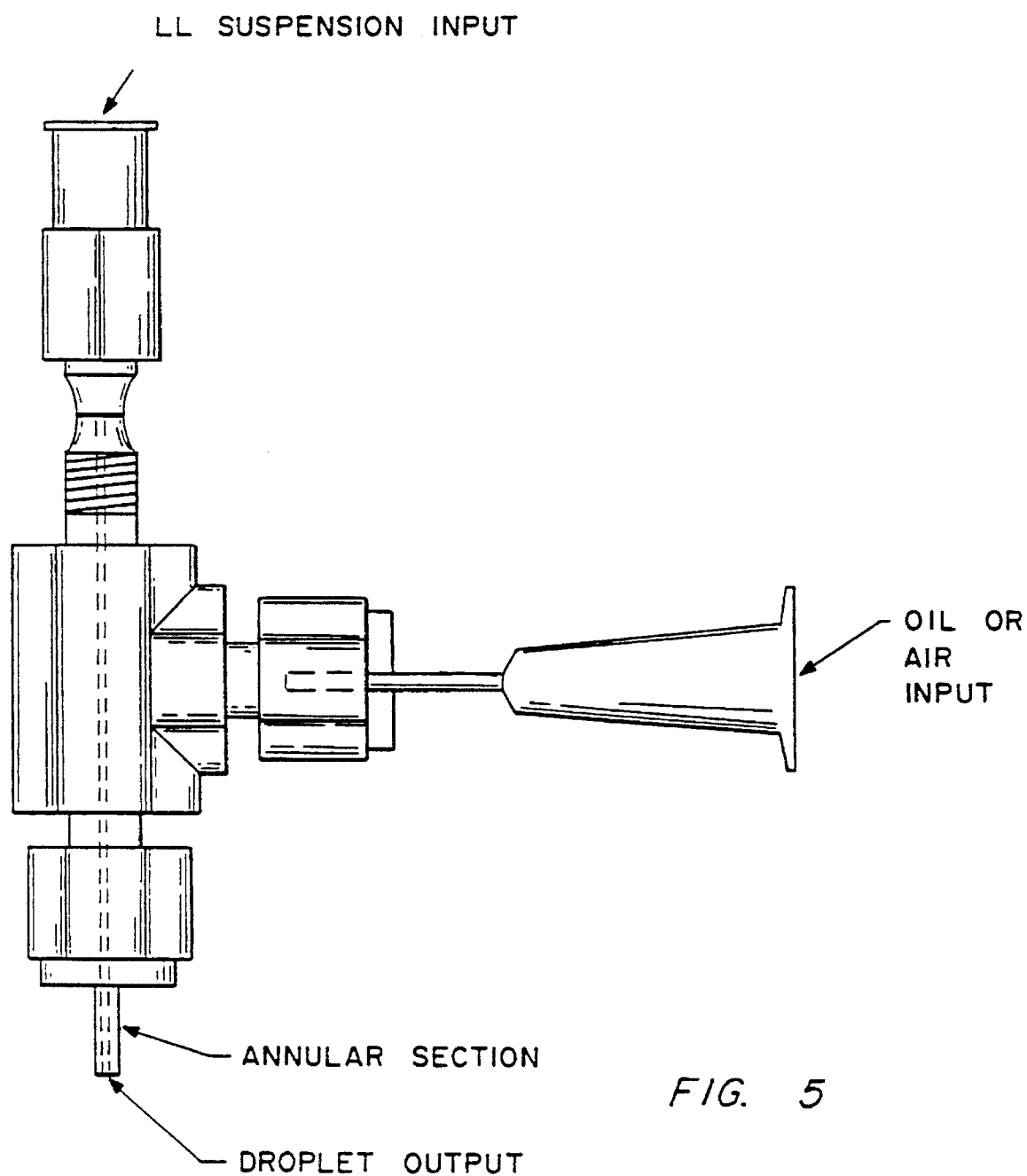
FIG. 5 is a representation of a co-extrusion of an air flow apparatus for use in mixing a 20 to 30% solution of macromer with a cell suspension and ethyl eosin and triethanolamine initiating system before exposure to laser light.

PEG diacrylates of different molecular weight were synthesized by a reaction of acryloyl chloride with PEG as in Example 1. A 20 to 30% solution of macromer was mixed with a cell suspension and the ethyl eosin and triethanolamine initiating system before exposing it to laser light through a coextrusion air flow apparatus, FIG. 5. Microspheres were prepared by an air atomization process in which a stream of macromer was atomized by an annular stream of air. The air flow rate used was 1,600 cc/min and macromer flow-rate was 0.5 mL/min. The droplets were allowed to fall to a petri dish containing mineral oil and were exposed to laser light for about 0.15 sec each to cause polymerization and make them insoluble in water. Microspheres so formed were separated from the oil and thoroughly washed with PBS buffer to remove unreacted macromer and residual initiator. The size and shape of microspheres was dependent on extrusion rate (0.05 to 0.1 mL/min) and extruding capillary diameter (18 Ga to 25 Ga). The polymerization times were dependent on initiator concentration (ethyl eosin concentration (5 $\mu$M to 0.5 mM), vinyl pyrrolidone concentration (0.0% to 0.1%), triethanolamine concentration (5 to 100 mM), laser power (10 mW to 1 W), and macromer concentration (>10% w/v).

Figure 6:
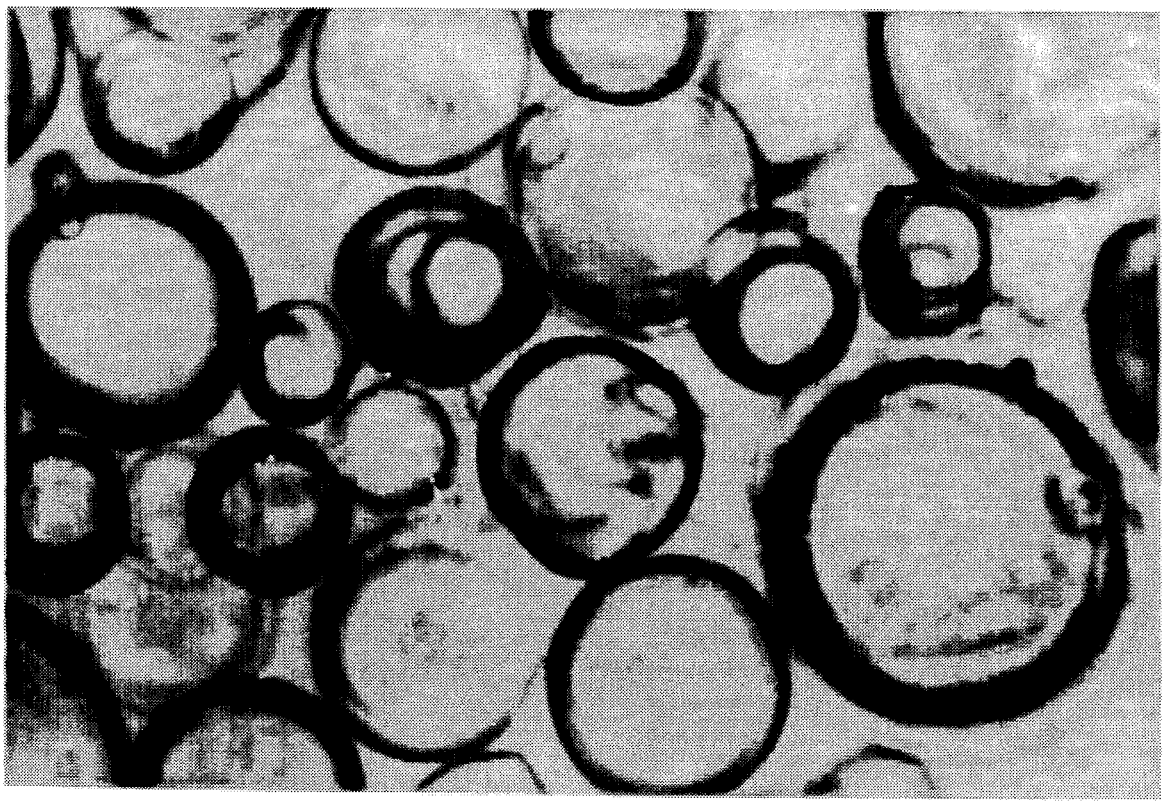
FIG. 6 shows spheres prepared using an air atomization process as described in Example 6 with a PEG diacrylate macromer of molecular weight 400 Da and a 30% solution in PBS, containing 0.1M triethanolamine as a cocatalyst and 0.5 mM ethyl eosin as a photoinitiator.

A PEG diacrylate macromer of molecular weight 400 Da was used as a 30% solution in PBS, containing 0.1M triethanolamine as a cocatalyst and 0.5 mM ethyl eosin as a photoinitiator. Spheres prepared using this method are shown in FIG. 6. The polymerizations were carried out at physiological pH in the presence of air. This is significant since radical polymerizations may be affected by the presence of oxygen, and the acrylate polymerization is still rapid enough to proceed effectively.

The process also works at lower temperatures. For cellular encapsulation, a 23% solution of PEO diacrylate was used with initiating and polymerization conditions as used in the air atomization technique. Cell viability subsequent to encapsulation was checked by trypan blue exclusion assay. Human foreskin fibroblasts (HFF), Chinese hamster ovary cells (CHO-K1), and a beta cell insuloma line (RiN5F) were found to be viable (more than 95%) after encapsulation. A wide range (>10%) of PEG diacrylate concentrations may be used equally effectively, as may PEG tetraacrylate macromers.

EXAMPLE 7

Coating of Animal Cell-Containing Alginate-PLL Microspheres and Individual Cells by Surface Dye Adsorption Alginate-PLL coacervated microspheres, containing animal cells, were suspended in a 1.1% $CaCl_2$ solution and were aspirated free of excess solution to obtain a dense plug of microspheres. A solution was filter sterilized by passage through a 0.45 pm filter. The plug of microspheres was suspended in 10 mL of eosin solution for 2 min to allow dye uptake. A solution of PEG 18.5 tetraacrylate (2 mL; 23% w/v) containing 100 $\mu$L of a 3.5 w/v solution of triethanolamine in HEPES buffered saline was added to 0.5 mL of these microspheres. The microspheres were exposed to an argon ion laser for 30 seconds with periodic agitation. The suspension of microspheres was uniformly scanned with the laser during this period. The microspheres were then washed with calcium solution and the process was repeated once more in order to attain a stable coating.

In order to verify survival of cells after the overcoat process, cells in suspension without the alginate/PLL microcapsule were exposed to similar polymerization conditions. 1 mL of lymphoblastic leukemia cells (RAJI) ($5\times10^5$ cells) was centrifuged at 300 g for 3 min. A 0.04% filter sterilized ethyl eosin solution in phosphate buffered saline (PBS) (1 mL) was added and the pellet was resuspended. The cells were exposed to the dye for 1 min and washed twice with PBS and then pelleted. Triethanolamine solution (10 $\mu$L; 0.1M) was added to the pellet and the tube was vortexed to resuspend the cells. 0.5 mL of PEO 18.5 kD tetraacrylate macromer was then mixed along with this suspension and the resulting mixture was exposed to an argon ion laser (514 nm, 50 mW) for 45 sec. The cells were then washed twice with 10 mL saline and once with media (RPMI 1640 with 10% FCS and 1% antibiotic, antimycotic). A thin membrane of PEO gel may be observed forming around each individual cell.

No significant difference in viability was seen between the control population (93% viable) and the treated cells (95% viable) by trypan blue exclusion. An assay for cell viability and function was performed by adapting the MTT-Formazan assay for the RAJI cells. This assay indicates >90% survival. Similar assays were performed with two other model cell lines. Chinese hamster ovary cells (CHO-K1) show no significant difference ($p<0.05$) in metabolic function as evaluated by the MTT-Formazan assay. 3T3 mouse fibroblasts also show no significant reduction ($p<0.05$) in metabolic activity.

EXAMPLE 8

Coating Animal Cell Containing Alginate-PLL Microspheres by the Oil Suspension Method Using the method described in Example 4, RAJI cells contained in alginate-PLL microspheres were coated with a PEG polymeric membrane. Viability of these cells was checked by trypan blue exclusion and they were found to be more than 95% viable.

EXAMPLE 9

Coating of Individual Islets of Langerhans by Surface Dye Adsorption

Using the method described in Example 7, ethyl eosin was adsorbed to the surfaces of islets, exposed to a solution of the PEG macromer with triethanolamine, and exposed to light from an argon-ion laser to form a thin PEG polymeric membrane on the surface of the islets. Islet viability was demonstrated by lack of staining with propidium iodide.

EXAMPLE 10

Biocompatibility of PEO on Microspheres

Figure 7A:
FIG. 7A shows a photograph of alginate-poly(L-lysine) microspheres explanted after 4 days.
Figure 7B:
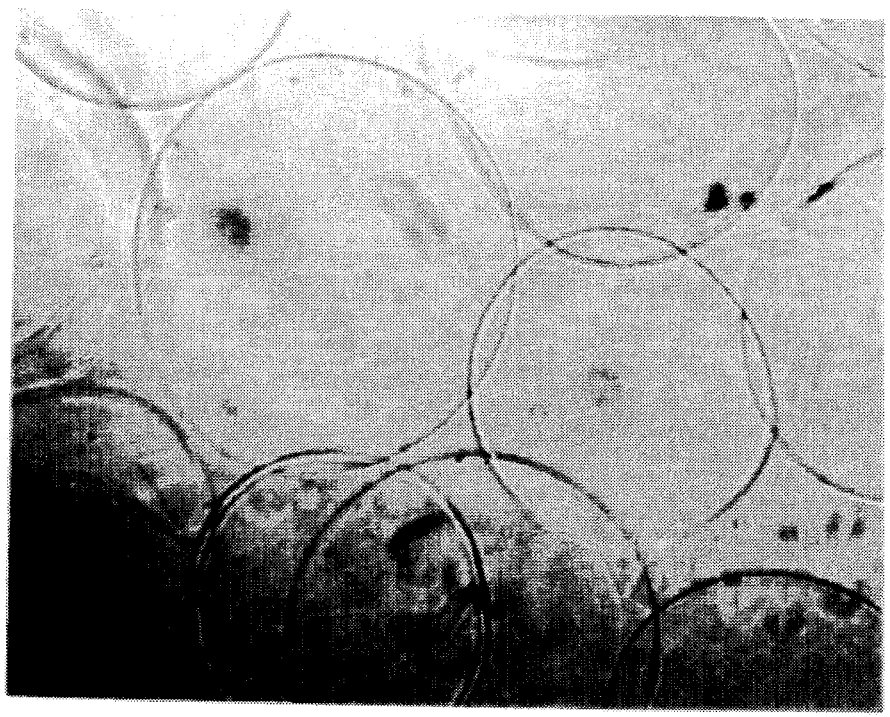
FIG. 7B shows spheres similar to those shown in FIG. 7A which had been coated with PEG gel by the dye diffusion precess before implantation.

In vivo evaluation of the extent of inflammatory response to microspheres prepared in Examples 7 and 8 was carried out by implantation in the peritoneal cavity of mice. Approximately 0.5 mL of microspheres were suspended in 5 mL of sterile HEPES buffered saline. A portion of this suspension (2.5 mL) was injected into the peritoneal cavity of ICR male Swiss white mice. The microspheres were recovered after 4 days by conducting a lavage of the peritoneal cavity with 5 mL of 10 U heparin/mL PBS. The extent of cellular growth on the microspheres was visually inspected under a phase contrast microscope. The number of unattached cells present in the recovered lavage fluid was counted using a Coulter counter. FIG. 7A shows a photograph of alginate-poly(L-lysine) microspheres explanted after 4 days, while FIG. 7B shows similar spheres which had been coated with PEG gel by the dye diffusion process before implantation. As expected, bilayer alginate-polylysine capsules not containing an outer alginate layer to provide an extreme test of the ability of the PEG gel layer to enhance the biocompatibility of the bilayer membrane, were completely covered with cells due to the highly cell adhesive nature of the PLL surface, whereas the PEG coated microspheres were virtually free of adherent cells. Almost complete coverage of alginate-poly(L-lysine) was expected because polylysine has amino groups on the surface, and positively charged surface amines can interact with cell surface proteoglycans and support cell growth (Reuveny, et al., 1983). The photographs in FIG. 7B strongly indicate that the highly charged and cell adhesive surface of PLL is covered by a stable layer of PEG gel. The integrity of the gel did not appear to be compromised.

The non-cell-adhesive tendency of these microspheres was evaluated as a percentage of the total microsphere area which appears covered with cellular overgrowth. These results are summarized in Table 3.

TABLE 3

| Microsphere Coverage with Cell Overgrowth | |
|---|---|
| Composition of PEG gel | % Cell coverage |
| 18.5 kD | <1 |
| 18.5 kD 90%:0.4 kD 10% | <1 |
| 18.5 kD 50%:0.4 kD 50% | <1 |
| 35k 90%:0.4 kD 10% | 5–7 |
| 35k 50%:0.4 kD 50% | <1 |
| Alginate poly(L-lysine) | 60–80 |

Figure 8:
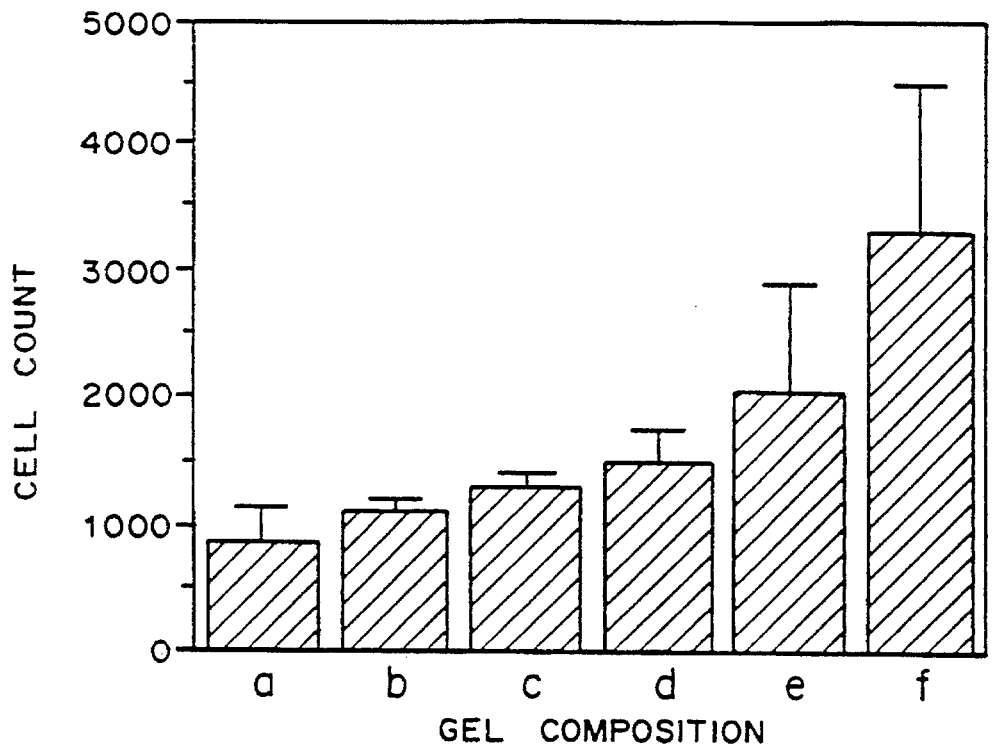
FIG. 8 shows a graphical representation of the variation of cell counts with chemical composition of the microsphere overcoat, A–F.

An increase in cell count was a result of activation of resident macrophages which secrete chemical factors such as interleukins and induce nonresident macrophages to migrate to the implant site. The factors also attract fibroblasts responsible for collagen synthesis. The variation of cell counts with chemical composition of the overcoat is shown FIG. 8 (A–F). It can be seen from the figure that all PEG coated spheres have substantially reduced cell counts. This is consistent with the PEG overcoat generally causing no irritation of the peritoneal cavity.

However, PEG composition does make a difference in biocompatibility, and increasing molecular weights were associated with a reduction in cell counts. This could be due to the gels made from higher molecular weight oligomers having higher potential for steric repulsion due to the longer chain lengths.

EXAMPLE 11

Permeability of PEO Gels

Figure 9:
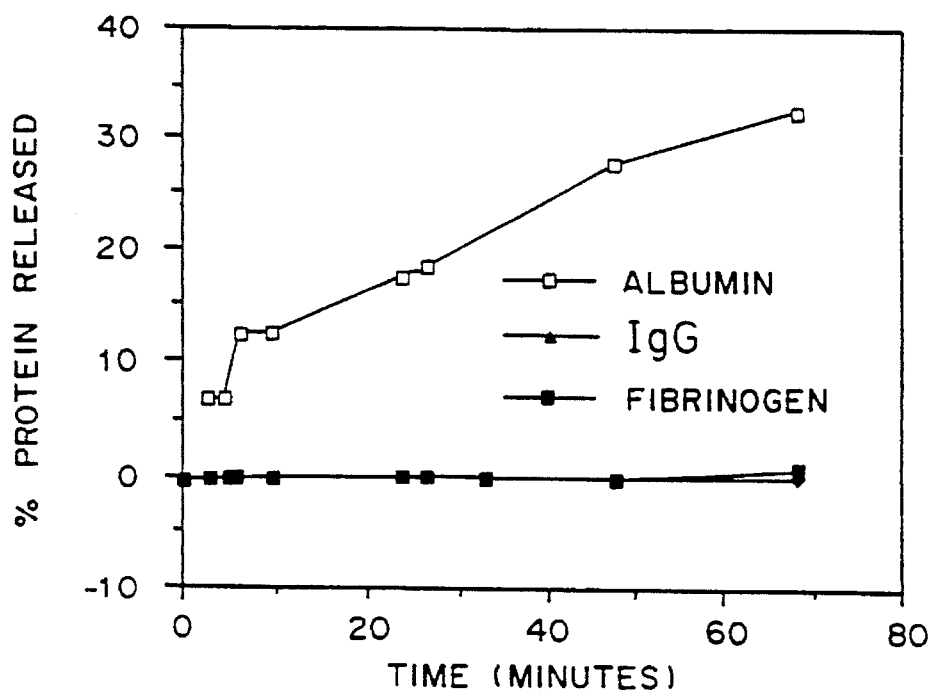
FIG. 9 shows permeability of PEO gels by a typical release profile for a PEO 18.5 kD gel.

Bovine serum albumin, human IgG, or human fibrinogen (20 mg) was dissolved in 2 mL of a 23% w/v solution of oligomeric PEO 18.5 kD tetraacrylate in PBS. This solution was laser polymerized to produce a gel 2 cm×2 cm×0.5 cm in size. The diffusion of bovine serum albumin, human IgG and human fibrinogen (mol wt 66 kD, 150 kD and 350 kD respectively) was monitored through the 2 cm×2 cm face of these gels using a total protein assay reagent (Biorad). A typical release profile for a PEO 18.5 kD gel is shown in FIG. 9. This gel allowed a slow transport of albumin but did not allow IgG and fibrinogen to diffuse. This indicates that these gels are capable of being used as immunoprotective barriers. This is a vital requirement for a successful animal tissue microencapsulation material.

Figure 10:
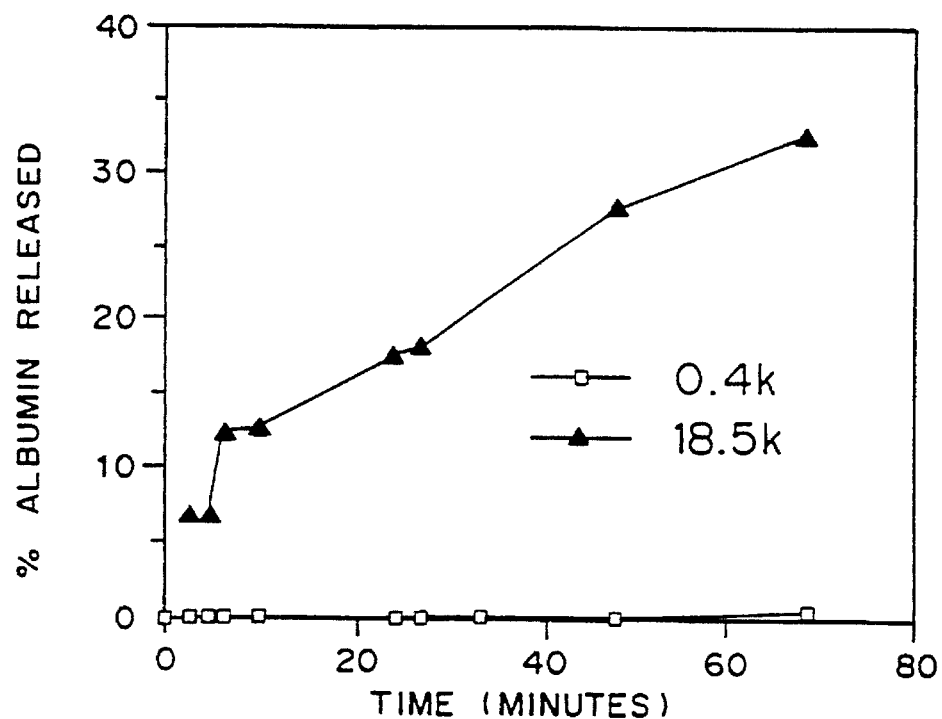
FIG. 10 shows the release of BSA through gels made from 23 % solutions of PEO diacrylate, s and tetraacrylates of 0.4 kD and 18.5 kD, respectively.

The release profile was found to be a function of crosslink density and molecular weight of the polyethylene glycol segment of the monomer. FIG. 10 shows the release of BSA through gels made from 23% solutions of PEO diacrylates and tetraacrylates of 0.4 kD and 18.5 kD, respectively. It is evident that the 18.5 kD gel is freely permeable to albumin while the 0.4 kD gel restricted the diffusion of albumin. The release of any substance from these gels will depend on the crosslink density of the network and will also depend on the motility of the PEG segments in the network. This effect is also dependent upon the functionality of the macromer. For example, the permeability of a PEG 18.5 kD tetraacrylate gel is less than that of an otherwise similar PEG 20 kD diacrylate gel.

In the case of short PEO chains between crosslinks, the "pore" produced in the network will have relatively rigid boundaries and will be relatively small and so a macromolecule attempting to diffuse through this gel will be predominantly restricted by a sieving effect. If the chain length between crosslinks is long, the chain can fold and move around with a high motility and, besides the sieving effect, a diffusing macromolecule will also encounter a free volume exclusion effect.

Due to these two contrasting effects a straightforward relation between molecular weight cutoff for diffusion and the molecular weight of the starting oligomer is not completely definable. Yet, a desired release profile for a particular protein or a drug such as a peptide may be accomplished by adjusting the crosslink density and length of PEG segments. Correspondingly, a desired protein permeability profile may be arranged to permit the diffusion of nutrients, oxygen, carbon dioxide, waste products, hormones, growth factors, transport proteins, and released cellularly synthesized proteins, while restricting the diffusion of antibodies and complement proteins and also the ingress of cells, to provide immunoprotectivity to transplanted cells or tissue. The three dimensional crosslinked covalently bonded polymeric network is chemically stable for long-term in vivo applications.

EXAMPLE 12

Treatment of Silicone Rubber to Enhance Biocompatibility

Pieces of medical grade silicone rubber (2×2 cm) were soaked for 1 h in benzene containing 23% 0.4 kD PEG diacrylate and 0.5% 2,2-dimethoxy-2-phenyl acetophenone. The thus swollen rubber was irradiated for 15 min with a long wave UV lamp (365 nm). After irradiation, the sample was rinsed in benzene and dried. The air contact angles of silicone rubber under water were measured before and after treatment. The decreased contact angle of 500 after treatment, over the initial contact angle of 630 for untreated silicone rubber reflects an increased hydrophilicity due to the presence of the PEG gel on the rubber surface.

This technique demonstrates that macromer polymerization can be used to modify a polymer surface so as to enhance biocompatability. For instance, a polyurethane catheter can be treated by this method to obtain an implantable device coated with PEG. The PEG was firmly anchored to the surface of the polyurethane catheter because the macromer was allowed to penetrate the catheter surface (to a depth of 1-2 microns) during the soaking period before photopolymerization. Upon irradiation, an interpenetrating network of PEG and polyurethane results. The PEG was thereby inextricably intertwined with the polyurethane.

EXAMPLE 13

Treatment of Polyurethane

INTRACATH (Becton Dickinson) polyurethane intravenous catheters (19 ga) were modified at their outer surfaces with polyethylene glycol diacrylate (PEG DA) of molecular weight 400 and 10000 The prepolymer was dissolved in tetrahydrofuran (THF), a solvent for the polyurethane, at 50° C., where polyurethane dissolution is relatively slow. The following solution was prepared and warmed to 50° C.:

| PEG DA (MW 400) | 15% |
| PEG DA (MW 10000) | 15% |
| THF | 70% | with 2,2-dimethoxy, 2-phenyl actophenone at 1.6% of the above solution.

2.5" length catheter segments were closed at one end by melting a 2 mm length by pressing with a hot metal spatula to from a flat tab. This tab was used to fix the catheter in the vessel wall in subsequent animal experiments. The catheter was held with forceps at the tab end and dipped in the treatment solution for 1-3 sec, pulled out, and the excess fluid shaken off. The treated catheter was illuminated with an ultraviolet light (Black Ray, 360 nm) for 2-3 min, rotating the catheter. An untreated control was similarly treated in 70% THF with 30% water replacing the PEG in the treatment solution.

Following this treatment, both the treated and control catheters were transferred to 100% methylene chloride to extract unreacted materials; this extraction was carried out for 36 hr with solvent replacement every 6 hr. These catheters were then dried and transferred to 70% ethanol, and then into water before use.

A second composition was also investigated:

| PEG DA (MW 400) | 10% |
| PEG DA (MW 10000) | 15% |
| Polyethylene oxide (MW 100,000) | 5% |
| THF | 70% | with 2,2-dimethoxy, 2-phenyl acetophenone at 1.6% of the above solution.

In this case, the polyethylene oxide of mw 100,000 was not a prepolymer and was immobilized within the PEG DA matrix by entanglement, rather than by chemical attachment.

Adult New Zealand male rabbits (7–10 lb) were anesthetized with rompun-acepromazien-ketamine. The animal was shaved on the ventrolateral jugular and the vessel was raised. A catheter was inserted into the vessel with the tab outside, and tied in place via the tab with 4.0 nylon to the adventitia. The catheter was inserted 1.5 to 2.0" into the vessel. The skin incision was closed.

After a period of 3 days, the animals were euthanized by overdose of pentobarbital intraperitoneally. The vessel was again raised and flushed with phosphate buffered saline (PBS) to superficially rinse away blood between the catheter and the vessel wall. Two 500 ml bottles, one filled with PBS and one with formalin in PBS were hung from an i.v. pole scaffold, and the hydraulic differential was used to perfusion fix the vessel. The vessels were removed proximal and distal to the ends of the catheters.

The treated catheters were completely wettable, and were very slippery.

A total of 12 rabbits were catheterized for 72 hr. Six were control, unmodified catheters. These catheters could not be removed from the vessel wall without dissection, i.e. they were tightly incorporated into the vessel. These catheters upon removal were red, and the vessel was barely patent. By contrast, the treated catheters were easily removable, the vessels were clearly patent, and the catheters were not red. Under the light microscope, a small amount of white thrombus could be seen on both formulations of the catheter coating, with somewhat lesser amounts on the formulation containing the polyethylene oxide 100,000.

EXAMPLE 14

Treatment of Ultrafiltration Membranes

The processes of Examples described above can be applied to the treatment of macrocapsular surfaces, such as those used for ultrafiltration, hemodialysis and non-microencapsulated immunoisolation of animal tissue. The macrocapsule in this case will usually be microporous with a molecular weight cutoff below 70,000 Da. It may be in the form of a hollow fiber, a spiral module, a flat sheet or other configuration. The surface of such a macrocapsule can easily be modified using the PEO gel coating process to produce a non-fouling, non-thrombogenic, and non-cell-adhesive surface. The coating serves to enhance biocompatibility and to offer additional immunoprotection. Materials which can be modified in this manner include polysulfones, cellulosic membranes, polycarbonates, polyamides, polyimides, polybenzimidazoles, nylons, and poly(acrylonitrile-co-vinyl chloride) copolymers and the like.

Depending on the physical and chemical nature of the surface a variety of methods can be employed to form biocompatible overcoats. Hydrophilic surfaces can simply be coated by applying a thin layer of a 30% w/v polymerizable solution of PEG diacrylate containing appropriate amounts of dye and amine. Hydrophobic surfaces can be first rendered hydrophilic by gas plasma discharge treatment and the resulting surface can then be similarly coated, or they may simply be treated with a surfactant before or during treatment with the PEG diacrylate solution.

EXAMPLE 15

Treatment of Textured Materials and Hydrogels

The surface of materials having a certain degree of surface texture, such as woven dacron, dacron velour, and expanded poly(tetrafluoroethylene) (ePTFE) membranes, was treated using the coating method described herein. Textured and macroporous surfaces allow greater adhesion of the PEG gel to the material surface. This allows the coating of relatively hydrophobic materials such as PTFE and poly(ethylene terepthalate) (PET).

Implantable materials such as enzymatic and ion sensitive electrodes, having a hydrogel (such as poly (HEMA), crosslinked poly(vinyl alcohol) and poly(vinyl pyrrolidone)) on their surface, are coated with the more biocompatible PEO gel in a manner similar to the dye adsorption and polymerization technique used for the alginate-PLL microspheres.

EXAMPLE 16

Treatment of Dense Materials

The surfaces of dense (e.g., nontextured, nongel) materials such as polymers (including PET, PTFE, polycarbonates, polyamides, polysulfones, polyurethanes, polyethylene, polypropylene, polystyrene), glass, and ceramics can be treated with PEO gel coatings. Hydrophobic surfaces were initially treated by a gas plasma discharge to render the surface hydrophilic. This ensures better adhesion of the PEO gel coating to the surface. Alternatively, coupling agents may be used to increase adhesion, as readily apparent to those skilled in the art of polymer synthesis.

EXAMPLE 17

Rate of Polymerization

Figure 11A:
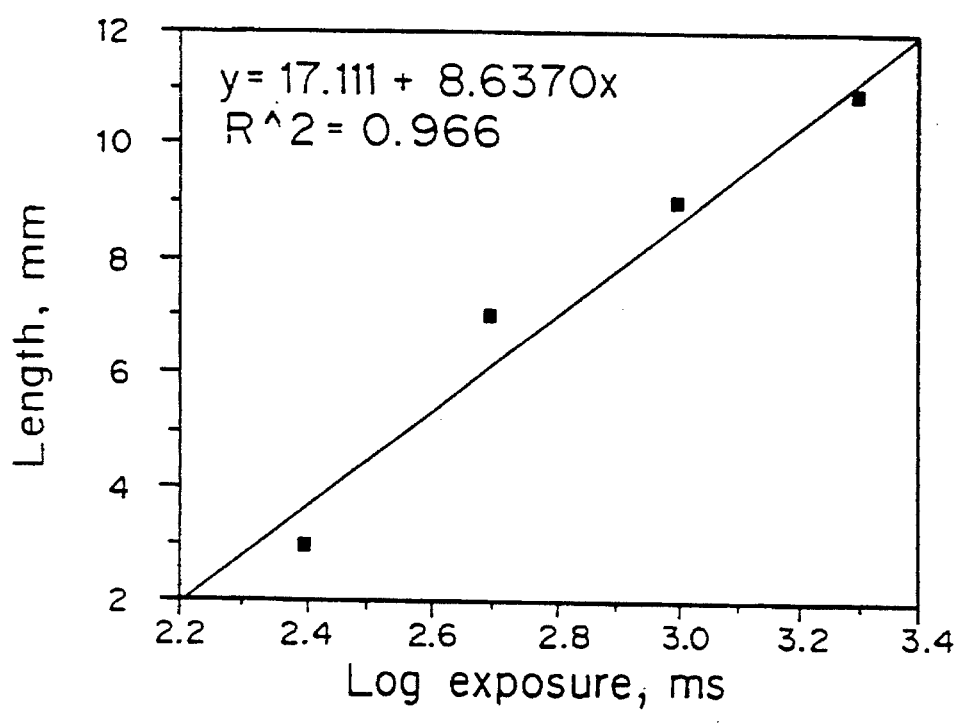
FIG. 11A shows a plot of the length of the spike of gel formed by penetration of the laser beam into the gel versus laser irradiation time.
Figure 11B:
FIG. 11B shows the spikes formed as a result of laser light penetration into the macromer.

To demonstrate rapidity of gelation in laser-initiated polymerizations of multifunctional acrylic monomers, the kinetics of a typical reaction were investigated. Trimethylolpropyl triacrylate containing $5\times10^{-4}$M ethyl eosin as a photoinitiator in 10 µmoles of N-vinyl pyrrolidone per mL of macromer mix and 0.1M of triethanolamine as a cocatalyst, was irradiated with a 500 mW argon ion laser (514 nm wavelength, power $3.05\times10^5$ W/m$^2$, beam diameter 1 mm, average gel diameter produced 1 mm). A plot of the length of the spike of gel formed by penetration of the laser beam into the gel versus laser irradiation time is shown in FIG. 11A. The spikes formed as a result of laser light penetration into the macromer can be seen in FIG. 11B.

A 23% w/w solution of various macromers in HEPES buffered saline containing 3 µL of initiator solution (300 mg/mL of 2,2-dimethoxy-2-phenylacetophenone in N-vinyl pyrrolidone) was used. 100 µL of the solution was placed on a glass coverslip and irradiated with a low intensity long wave UV (LWUV) lamp (BlakRay, model 3–100A with flood). The times required for gelation to occur were noted and are given in Table 4. These times were typically in the range of 10 seconds.

TABLE 4

Gelling Time

| Polymer Code | Gel Time (sec) (mean ± S.D.) |
| --- | --- |
| 0.4 kD | 6.9 ± 0.5 |
| 1 kD | 21.3 ± 2.4 |
| 6 kD | 14.2 ± 0.5 |
| 10 kD | 8.3 ± 0.2 |
| 18.5 kD | 6.9 ± 0.1 |
| 20 kD | 9.0 ± 0.4 |

Time periods of about 10–100 ms were sufficient to gel a 300 µm diameter droplet (a typical size of gel used in microencapsulation technology). This rapid gelation, if used in conjunction with proper choice of macromers, can lead to entrapment of living cells in a three dimensional covalently bonded polymeric network. The monochromatic laser light will not be absorbed by the cells unless a proper chromophore is present, and is considered to be harmless if wavelength is more than about 400 nm. Exposure to long wavelength ultraviolet light (>360 nm) is harmless at practical intensities and durations.

EXAMPLE 18

PEO Gel Interactions

Biocompatibility with HFF (human foreskin fibroblasts) cells was demonstrated as follows.

Figure 12A:
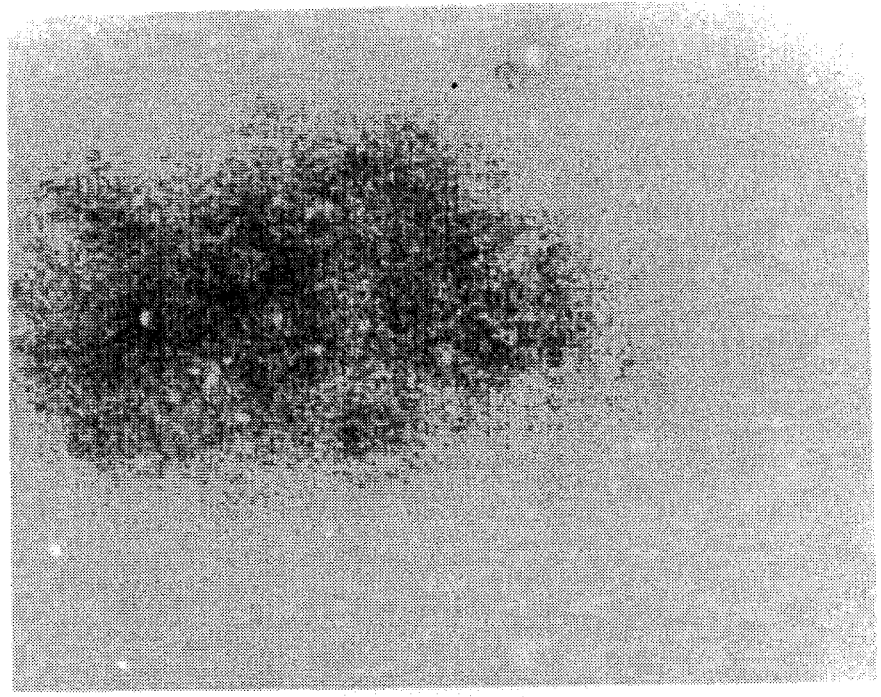
FIG. 12A shows a phase contrast micrograph of the growth of HFF cells on a typical PEG gel as compared to glass surface (FIG. 12B).
Figure 12B:
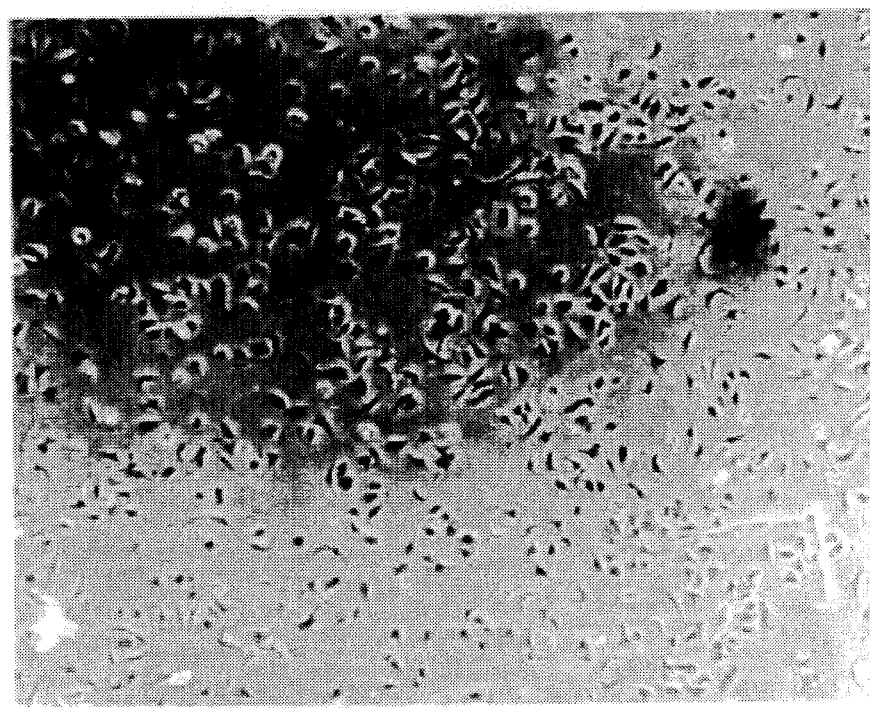
FIG. 12B shows a phase contrast micrograph of the growth of HFF cells on a glass surface.

HFF cells were seeded on PEO 18.5 kD tetraacrylate gels at a density of 18,000 cells/cm$^2$ in Dulbecco's modification of Eagle's medium containing 10% fetal calf serum. The gels were then incubated at 37° C. in a 5% CO$_2$ environment for 4 hr. At the end of this time the gels were washed with PBS to remove any non-adherent cells and were observed under a phase contrast microscope at a magnification of 200×. FIG. 12A shows the growth of these cells on a typical PEG gel as compared to glass surface (FIG. 12B). The number of attached cells/cm$^2$ was found to be 510±170 on the gel surfaces as compared to 13,200±3,910 for a control glass surface. The cells on these gels appeared rounded and were not in their normal spread morphology, strongly indicating that these gels do not encourage cell attachment.

Figure 13:
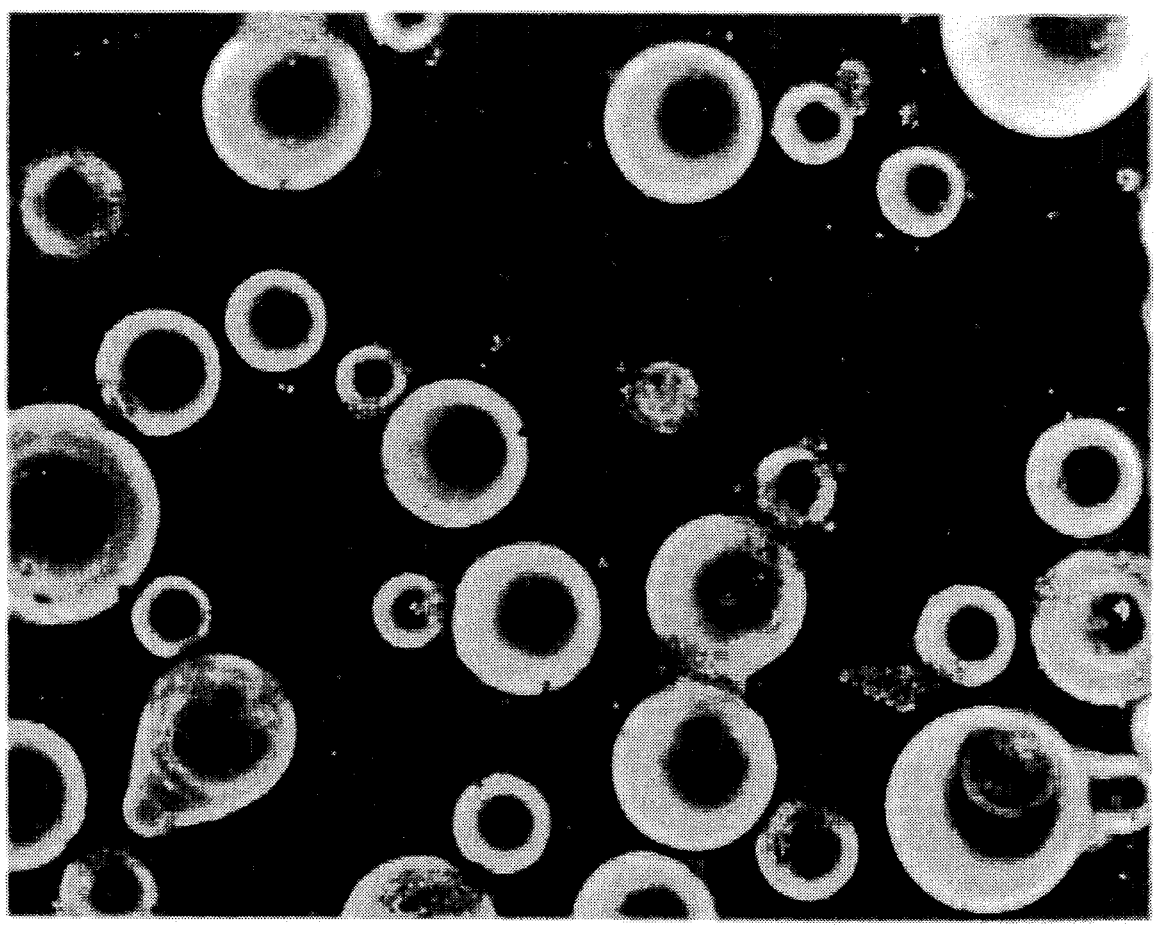
FIG. 13 shows a photograph of microspheres explanted from mice as in Example 10.

Biocompatibility on microspheres was demonstrated as follows. FIG. 13 shows a photograph of microspheres explanted from mice as in Example 10; after 4 days very little fibrous overgrowth was seen. The resistance of PEG chains to protein adsorption and hence cellular growth was well documented. Table 5 summarizes the extent of cellular overgrowth seen on these microspheres after 4 day intraperitoneal implants for various PEG diacrylate gels.

TABLE 5

| PEG Diacrylate for Gels (mol wt, Daltons) | Extent of Cellular Overgrowth |
| --- | --- |
| 400 | 5–10% |
| 1,000 | 15–25% |
| 5,000 | 3–5% |

TABLE 5-continued

| PEG Diacrylate for Gels (mol wt, Daltons) | Extent of Cellular Overgrowth |
|---|---|
| 6,000 | 2–15% |
| 10,000 | 10–20% |
| 18,500 | 4–10% |

EXAMPLE 19

Characterization and Mechanical Analysis of PEO Gels

Solutions of PEO diacrylates (23% w/v; 0.4 kD, 6 kD, 10 kD) and PEG tetraacrylates (18.5 kD) were used. An initiator solution (10 μL) containing 30 mg/mL of 2,2-dimethoxy-2-phenyl acetophenone in vinyl-2-pyrrolidone was used per mL of the macromer solution. The solution of initiator containing macromer was placed in a 4.0×1.0×0.5 cm mold and exposed to a long wave ultraviolet lamp (365 nm) for approximately 10 seconds to induce gelation. Samples were allowed to equilibrate in phosphate buffered saline (pH 7.4) for 1 week before analysis 1 performed.

A series of "dogbone" samples (samples cut from a slab into the shape of a dogbone, with wide regions at both ends and a narrower long region in the middle) were cut for ultimate tensile strength tests. Thickness of the samples was defined by the thickness of the sample from which they were cut. These thicknesses ranged from approximately 0.5 mm to 1.75 mm. The samples were 20 mm long and 2 mm wide at a narrow "neck" region. The stress strain tests were run in length control at a rate of 4% per second. After each test, the cross sectional area was determined. Table 6 shows the ultimate tensile strength data. It is seen that the lower molecular weight macromers in general give stronger gels which were less extensible than those made using the higher molecular weight macromers. The PEG 18.5 kD tetraacrylate gel is seen to be anomalous in this series, resulting from the multifunctionality of the macromer and the corresponding higher crosslinking density in the resulting gel. This type of strengthening result could be similarly achieved with macromers obtained having other than four free radical sensitive groups, such as acrylate groups.

TABLE 6

Gel strength Tests

| | PEO Acrylate Precursor Molecular Weight | | | |
|---|---|---|---|---|
| | 0.4 kD | 6 kD | 10 kD | 18.5 kD |
| Stress (kPa)* | 168+/−51 | 98+/−15 | 33+/−7 | 115+/−56 |
| % Strain* | 8+/−3 | 71+/−13 | 110+/−9 | 40+/−15 |
| Slope* | 22+/−5 | 1.32+/−0.31 | 0.27+/−0.04 | 2.67+/−0.55 |

*Values are mean+/−S.D.

For the creep tests, eight samples approximately 0.2× 0.4×2 cm were loaded while submersed in saline solution. They were tested with a constant unique predetermined load for one hour and a small recovery load for ten minutes. Gels made from PEG diacrylates of 1 kD, 6 kD, and 10 kD, and PEG tetraacrylates of 18.5 kD PEO molecular weight were used for this study. The 10 kD test wets terminated due to a limit error (the sample stretched beyond the travel of the loading frame). The 1 kD sample was tested with a load of 10 g and a recovery load of 0.2 g. The 6 kD sample was tested at a load of 13 g with a recovery load of 0.5 g. The 18.5 kD sample was tested at a load of 13 g with a recovery load of 0.2 g. The choice of loads for these samples produced classical creep curves with primary and secondary regions.

EXAMPLE 20

Water Content of PEO Gels

Solutions of various macromers were made as described above. Gels in the shape of discs were made using a mold. The solutions (400 μL) was used for each disc. The solutions were irradiated for 2 minutes to ensure thorough gelation. The disc shaped gels were removed and dried under vacuum at 60° C. for 2 days. The discs were weighed (WI) and then extracted repeatedly with chloroform for 1 day. The discs were dried again and weighed (W2). The gel fraction was calculated as W2/W1. This data appears in Table 7.
Determination of Degree of Hydration Subsequent to extraction, the discs were allowed to equilibrate with HBS for 6 hours and weighed (W3) after excess water had been carefully swabbed away. The total water content was calculated as (W3−W2)×100/W3. The data for gel water contents is summarized in the following table.

TABLE 7

| Polymer Coat | % Total Water | % Gel content |
|---|---|---|
| 0.4 kD | — | 99.8 ± 1.9 |
| 1 kD | 79.8 ± 2.1 | 94.5 ± 2.0 |
| 6 kD | 95.2 ± 2.5 | 69.4 ± 0.6 |
| 10 kD | 91.4 ± 1.6 | 96.9 ± 1.5 |
| 18.5 kD | 91.4 ± 0.9 | 80.3 ± 0.9 |
| 20 kD | 94.4 ± 0.6 | 85.0 ± 0.4 |

EXAMPLE 2

Mechanical Stability of PEO Gels after Implantation

PEG diacrylate (10 kD) and PEG—tetraacrylate (18.5 kD) were cast in dogbone shapes as described in Example 19. PEG-dacrylate or tetraacrylate (23% w/w) in sterile HEPES buffered saline (HBS) (0.9% NaCl, 10—HEPES, pH 7.4) containing 900 ppm of 2,2-dimethoxy-2-phenoxyacetophenone as initiator, was poured into an aluminum mold and irradiated with a LWUV lamp (Black ray) for 1 min. The initial weights of these samples were found after oven-drying these gels to constant weight. The samples were soxhlet-extracted with methylene chloride for 36 hours in order to leach out any unreacted prepolymer from the gel matrix (sol-leaching) prior to testing. The process of extraction was continued until the dried gels gave constant weight.

ICR Swiss male white mice, 6–8 weeks old (Sprague-Dawley), were anesthetized by an intraperitoneal injection of sodium pentobarbital. The abdominal region of the mouse was shaved and prepared with betadine. A ventral midline incision 10–15 mm long was made. The polymer sample, fully hydrated in sterile PBS (Phosphate buffered saline) or HEPES buffered saline (for calcification studies), was inserted through the incision and placed over the mesentery, away from the wound site. The peritoneal wall was closed with a lock stitched running suture (4.0 silk, Ethicon). The skin was closed with stainless steel skin staples, and a topical antibiotic (Furacin) was applied over the incision site. Three animals were used for each time point. One dogbone sample was implanted per mouse and explanted at the end of 1 week, 3 weeks, 6 weeks, and 8 weeks. Explanted gels were rinsed in HBS twice and then treated with 0.3 mg/mL pronase (Calbiochem) to remove any adherent cells and tissue. The samples were then oven-dried to a constant weight, extracted, and reswelled as mentioned before.

Tensile stress strain test was conducted on both control (unimplanted) and explanted dogbones in a small horizontal Instron-like device. The device is an aluminum platform consisting of two clamps mounted flat on a wooden board between two parallel aluminum guide. The top clamp was stationary while the bottom clamp was movable. Both the frictional surfaces of the moving clamp and the platform were coated with aluminum backed Teflon (Cole-Parmer) to minimize frictional resistance. The moving clamp was fastened to a device capable of applying a gradually increasing load. The whole set up was placed horizontally under a dissecting microscope (Reichert) and the sample elongation was monitored using a video camera. The image from the camera was acquired by an image processor (Argus-10, Hamamatsu) and sent to a monitor. After breakage, a cross section of the break surface was cut and the area measured. The load at break was divided by this cross section to find the maximum tensile stress. Table 8 lists the stress at fracture of PEG tetraacrylate (18.5 kD) hydrogels explanted at various time intervals. No significant change in tensile strength was evident with time. Thus, the gels appear mechanically stable to biodegradation in vivo within the maximum time frame of implant in mice.

TABLE 8

| TIME IMPLANTED | STRESS (KPa) (mean ± error*) | STRAIN AV. (mean ± error*) |
| --- | --- | --- |
| 1 WK | 52.8 ± 16.7 | 0.32 ± 0.19 |
| 3 WK | 36.7 ± 10.6 | 0.37 ± 0.17 |
| 6 WK | 73.3 ± 34.9 | 0.42 ± 0.26 |
| 8 WK | 34.1‡ | 0.30‡ |
| CONTROL | 44.9 ± 5.3 | 0.22 ± 0.22 |

*Error based on 90% confidence limits.
‡Single sample.

EXAMPLE 22

Monitoring of Calcification of PEO Gels

Disc shaped PEG-tetraacrylate hydrogels (m.w. 18.5 kD) were implanted intraperitoneally in mice as mentioned above for a period of 1 week, 3 weeks, 6 weeks, or 8 weeks. Explanted gels were rinsed in HBS twice and treated with Pronase (Calbiochem) to remove cells and cell debris. The samples were then equilibrated in HBS to let free $Ca^{++}$ diffuse out from the gel matrix. The gels were then oven-dried (Blue-M) to a constant weight and transferred to Aluminum oxide crucibles (COORS, high temperature resistant). They were incinerated in a furnace at 700° C. for at least 16 hours. Crucibles were checked for total incineration, if any residual remnants or debris was seen they were additionally incinerated for 12 hours. Subsequently, the crucibles were filled with 2 mL of 0.5M HCl to dissolve $Ca^{++}$ salt and other minerals in the sample. This solution was filtered and analyzed with atomic absorption spectroscopy (AA) for calcium content.

Calcification data on PEG-tetraacrylate (mol. wt. 18.5 kD) gel implants is given in Table 9. No significant increase in calcification was observed up to an 8 week period of implantation in mice.

TABLE 9

| TIME (Days) | CALCIFICATION (mean ± error*) (mg Calcium/g of Dry gel wt.) |
| --- | --- |
| 7 | 2.33 ± 0.20 |
| 21 | 0.88 ± 0.009 |
| 42 | 1.08 ± 0.30 |
| 56 | 1.17 ± 0.26 |

*Error based on 90% confidence limits.

EXAMPLE 23

Encapsulation of Neurotransmitter-Releasing Cells

Paralysis agitans, more commonly called Parkinson's disease, is characterized by a lack of the neurotransmitter dopamine within the striatum of the brain. Dopamine secreting cells such as cells from the ventral mesencephalon, from neuroblastoid cell lines or from the adrenal medulla can be encapsulated in a manner similar to that of other cells mentioned in prior Examples. Cells (including genetically engineered cells) secreting a precursor for a neurotransmitter, an agohist, a derivative or a mimic of a particular neurotransmitter or analogs can also be encapsulated.

EXAMPLE 24

Encapsulation of Hemoglobin for Synthetic Erythrocytes

Hemoglobin in its free form can be encapsulated in PEG gels and retained by selection of a PEG chain length and cross-link density which prevents diffusion. The diffusion of hemoglobin from the gels may be further impeded by the use of polyhemoglobin, which is a cross-linked form of hemoglobin. The polyhemoglobin molecule is too large to diffuse from the PEG gel. Suitable encapsulation of either native or crosslinked hemoglobin may be used to manufacture synthetic erythrocytes. The entrapment of hemoglobin in small spheres (<5 µm) of these highly biocompatible materials would lead to enhanced circulation times relative to crosslinked hemoglobin or liposome encapsulated hemoglobin.

Hemoglobin in PBS is mixed with the prepolymer in the following formulation:

| Hemoglobin at the desired amount | |
| --- | --- |
| PEG DA (MW 10000) | 35% |
| PEG DA (MW 1000) | 5% |
| PBS | 60% | with 2,2-dimethoxy, 2-phenyl acetophenone at 1.6% of the above solution.

This solution is placed in mineral oil at a ratio of 1 part hemoglobin/prepolymer solution to 5 parts mineral oil and is rapidly agitated with a motorized mixer to form an emulsion. This emulsion is illuminated with a long-wavelength ultraviolet light (360 nm) for 5 min to crosslink the PEG prepolymer to form a gel. The mw of the prepolymer may be selected to resist the diffusion of the hemoglobin from the gel, with smaller PEG DA molecular weights giving less diffusion. PEG DA of MW 10000, further crosslinked with PEG DA 1000, should possess the appropriate permselectivity to restrict hemoglobin diffusion, and it should possess the appropriate biocompatibility to circulate within the bloodstream.

EXAMPLE 25

Entrapment of Enzymes for Correction of Metabolic Disorders and Chemotherapy Congenital deficiency of the enzyme catalase causes acatalasemia. Immobilization of catalase in PEG gel networks could provide a method of enzyme replacement to treat this disease. Entrapment of glucosidase can similarly be useful in treating Gaucher's disease. Microspherical PEG gels entrapping urease can be used in extracorporeal blood to convert urea into ammonia. Enzymes such as asparaginase can degrade amino acids needed by tumor cells. Immunogenicity of these enzymes prevents direct use for chemotherapy. Entrapment of such enzymes in immunoprotective PEG gels, however, can support successful chemotherapy. A suitable formulation can be developed for either slow release or no release of the enzyme.

Catalase in PBS is mixed with the prepolymer in the following formulation:

| Catalase at the desired amount | |
|---|---|
| PEG DA (MW 10000) | 35% |
| PEG DA (MW 1000) | 5% |
| PBS | 60% | with 2,2-dimethoxy, 2-phenyl acetophenone at 1.6% of the above solution.

This solution is placed in mineral oil at a ratio of part catalase/prepolymer solution to 5 parts mineral oil and is rapidly agitated with a motorized mixer to form an emulsion. This emulsion is illuminated with a long-wavelength ultraviolet light (360 nm) for 5 min to crosslink the PEG prepolymer to form gel. The mw of the prepolymer may be selected to resist the diffusion of the catalase from the gel, with smaller PEG DA molecular weights giving less diffusion.

PEG DA of MW 10,000, further crosslinked with PEG DA 1000, should possess the appropriate permselectivity to restrict catalase diffusion, and it should possess the appropriate permselectivity to permit the diffusion of hydrogen peroxide into the gel-entrapped catalase to allow the enzymatic removal of the hydrogen peroxide from the bloodstream. Furthermore, it should possess the appropriate biocompatibility to circulate within the bloodstream.

In this way, the gel is used for the controlled containment of a bioactive agent within the body. The active agent (enzyme) is large and is retained within the gel, and the agent upon which it acts (substrate) is small and can diffuse into the enzyme rich compartment. However, the active agent is prohibited from leaving the body or targeted body compartment because it cannot diffuse out of the gel compartment.

EXAMPLE 26

Cellular Microencapsulation for Evaluation of Anti-Human Immunodeficiency Virus Drugs In Vivo HIV infected or uninfected human T-lymphoblastoid cells can be encapsulated into PEG gels as described for other cells above. These microcapsules can be implanted in a nonhuman animal and then treated with test drugs such as AZT or DDI. After treatment, the microcapsules can be harvested and the encapsulated cells screened for viability and functional normalcy using a fluorescein diacetate/ethidium bromide live/dead assay. Survival of infected cells indicates successful action of the drug. Lack of biocompatibility is a documented problem in this approach to drug evaluations, but the highly biocompatible gels described herein solve this problem.

EXAMPLE 27

Use of PEG Gels as Adhesive to Rejoin Severed Nerve

A formulation of PEG tetraacrylate (10%, 18.5 kD), was used as adhesive for stabilizing the sutureless apposition of the ends of transected sciatic nerves in the rat. Rats were under pentobarbital anesthesia during sterile surgical procedures. The sciatic nerve was exposed through a lateral approach by deflecting the heads of the biceps femoralis at the mid-thigh level. The sciatic nerve was mobilized for approximately 1 cm and transected with iridectomy scissors approximately 3 mm proximal to the tibeal-peroneal bifurcation. The gap between the ends of the severed nerves was 2–3 mm. The wound was irrigated with saline and lightly swabbed to remove excess saline. Sterile, unpolymerized PEG tetraacrylate solution was applied to the wound. Using delicate forceps to hold the adventitia or perineurium, the nerve ends were brought into apposition, the macromer solution containing 2,2-dimethoxy-2-phenylacetophenone as a photoinitiator and the wound was exposed to long wavelength UV-light (365 nm) for about 10 sec to polymerize the adhesive. The forceps were gently pulled away. Care was taken to prevent the macromer solution from flowing between the two nerve stumps. Alternatively, the nerve stump junction was shielded from illumination, e.g. with a metal foil, to prevent gelation of the macromer solution between the stumps; the remaining macromer solution was then simply washed away.

In an alternative approach, both ends of the transected nerve were held together with one pair of forceps. Forcep tips were coated lightly with petrolatum to prevent reaction with the adhesive. The polymerized adhesive serves to encapsulate the wound and adhere the nerve to the underlying muscle. The anastomosis of the nerve ends resists gentle mobilization of the joint, demonstrating a moderate degree of stabilization. The muscle and skin were closed with sutures. Reexamination after one month shows that severed nerves can remain reconnected, despite unrestrained activity of the animals.

EXAMPLE 28

Surgical Adhesive

The unpolymerized macromer mixture was an aqueous solution, such as that of PEO 400 kD diacrylate or PEO 18.5 kD tetraacrylate. When this solution contacts tissue which has a moist layer of mucous or fluid covering it, it intermixes with the moisture on the tissue. The mucous layer on tissue comprises water soluble polysaccharides which intimately contact cellular surfaces. These, in turn, are rich in glycoproteins and proteoglycans. Thus, physical intermixing, hydrogen bonding, and forces of surface interlocking due to penetration into crevices are some of the forces responsible for the adhesion of the PEO gel to a tissue surface subsequent to crosslinking.

PEO diacrylate solutions can therefore be used as tissue adhesives as in the previous example. Specific application is for such adhesives may include blood vessel anastomosis, soft tissue reconnection, drainable burn dressings, and retinal reattachment. However, if the PEO gel is polymerized away from tissue, it then presents a very non-adhesive surface to cells and tissue in general, due to the low interfacial energy intrinsic to the material.

Abdominal muscle flaps from female New Zealand white rabbits were excised and cut into strips 1 cm×5 cm. The flaps were approximately 0.5 to 0.8 cm thick. A lap joint (1 cm×1 cm) was made using two such flaps. Two different PEO di- and (tetra-) acrylate macromer compositions, 0.4 kD (di-) and 18.5 kD (tetra-), were evaluated. The 0.4 kD composition was a viscous liquid and was used without further dilution. The 18.5 kD composition was used as a 23% w/w solution in HBS. 125 μL of ethyl eosin solution in n-vinyl pyrrolidone (20 mg/mL) along with 50 μL of triethanolamine was added to each mL of the adhesive solution. 100 μL of adhesive solution was applied to each of the overlapping flaps. The lap joint was then irradiated by scanning with a 2 W argon ion laser for 30 seconds from each side. The strength of the resulting joints was evaluated by measuring the force required to shear the lap joint. One end of the lap joint was clamped and an increasing load was applied to the other end, while holding the joint horizontally until it failed. Four joints were tested for each composition. The 0.4 kD joints had a strength of 12.0±6.9 KPa (mean±S.D.), while the 18.5 kD joints had a strength of 2.7±0.5 KPa. It is significant to note that it was possible to achieve photopolymerization and reasonable joint strength despite the 6–8 mm thickness of tissue. A spectrophotometric estimate using 514 nm light showed less than 1% transmission through such muscle tissue.

EXAMPLE 29

Modification of PVA Polymer

Water soluble polymers other than PEG can also be modified using a similar chemical approach to that in prior examples. Thus, poly (vinyl alcohol) (PVA), which is water soluble, can be easily crosslinked to give a gel wherein the crosslinking occurs under conditions mild enough to permit gelation in contact with or in the vicinity of biological materials such as tissues, mammalian cells, proteins, or polysaccharides. The method adopted herein leads to PVA crosslinking under very mild conditions as compared to the standard techniques of formaldehyde crosslinking.

Polyvinyl alcohol (2 g; m.w. 100,000–110,000 D) was dissolved in 20 mL of hot DMSO. The solution was cooled to room temperature, and 0.2 mL of triethylamine and 0.2 mL of acryloyl chloride was added with vigorous stirring under an argon atmosphere. The reaction mixture was heated to 70° C. for 2 hr and cooled. The polymer was precipitated in acetone, redissolved in hot water, and precipitated again in acetone. Finally, it was dried under vacuum for 12 hr at 60° C. A solution of this polymer in PBS (5–10% w/v) was mixed with the UV photoinitiator and polymerized using long wavelength UV light to make microspheres 200–1,000 microns in size. These microspheres were stable to autoclaving in water, which indicates that the gel was covalently cross-linked. The gel was extremely elastic. This macromer, PVA multiacrylate, may be used to increase the crosslinking density in PEG diacrylate gels, with corresponding changes in mechanical and permeability properties. This approach could be pursued with any number of water-soluble polymers which are chemically modified with photopolymerizable groups; for example, with water-soluble polymers chosen from polyvinylpyrrolidone, polyethyloxazoline, polyethyleneoxide-polypropyleneoxide copolymers, polysaccharides such as dextran, alginate, hyaluronic acid, chondroitin sulfate, heparin, heparin sulfate, heparan sulfate, guar gum, gel Ian gum, xanthan gum, carrageenan gum, etc., and proteins such as albumin, collagen, gelatin, and the like.

EXAMPLE 30

Use of Alternative Photopolymerizable Moieties

Many photopolymerizable groups may be used to enable gelation. Several possibilities are shown below, based upon a PEG central chain:

$$CH_2=CH-F_2-R-F_1-(CH_2-CH_2-O)_n-(F_1-R-F_2-CH=CH_2)_m$$

with X substituents on the terminal CH groups.

where $F_1$=CONH, COO or NHCOO

X=H, $CH_3$, $C_2H_5$, $C_6H_5$, Cl, Br, OH or $CH_2COOH$ $F_2$=COO, CONH, O or $C_6H_4$,

R=$CH_2$ or -alkyl-, n≧5, and m≧3.

To illustrate a typical alternative synthesis, a synthesis for PEG 1 kD urethane methacrylate is described as follows, where $F_1$=NHCOO, $F_2$=COO, R=$CH_3$ and X=$CH_3$:

In a 250 mL round bottom flask, 10 g of PEG 1 kD was dissolved in 150 mL benzene. 2-isocyanatoethylmethacrylate (3.38 g) and 20 pL of dibutyltindilaurate were slowly introduced into the flask. The reaction was refluxed for 6 hours, cooled, and poured into 1000 mL hexane. The precipitate was filtered and dried under vacuum at 60° C. for 24 hours.

EXAMPLE 31

Use of Alternative Photoinitiator/Photosensitizer Systems

It is possible to initiate photopolymerization with a wide variety of dyes as initiators and a number of electron donors as effective cocatalysts. Table 10 illustrates photopolymerization initiated by several other dyes which have chromophores absorbing at widely different wavelengths. All gelations were carried out using a 23% w/w solution of 18.5 kD PEG tetraacrylate in HEPES buffered saline. These initiating systems compare favorably with conventional thermal initiating systems, as can also be seen from Table 10.

TABLE 10

Polymerization Initiation

| INITIATOR | LIGHT SOURCE* | TEMPERATURE °C. | APPROXIMATE GEL TIME, (SEC) |
|---|---|---|---|
| Eosin Y, 0.00015 M, Triethanolamine 0.65 M | S1 with UV filter | 25 | 10 |
| Eosin Y, 000015 M; Triethanolamine 0.65 M | S4 | 25 | 0.1 |
| Methylene Blue, 0.00024 M; p-toluenesulfonic acid, 0.0048 M | S3 | 25 | 120 |
| 2,2-dimethoxy-2-phenyl acetophenone 900 ppm | S2 | 25 | 8 |
| Potassium Persulfate 0.0168 M | — | 75 | 180 |
| Potassium Persulfate 0.0168 M; tetramethyl ethylene-diamine 0.039 M | — | 25 | 120 |
| Tetramethyl ethylene-diamine 0.039 M; Riboflavin 0.00047 M | S1 with UV filter | 25 | 300 |

*LIST OF LIGHT SOURCES USED

| CODE | SOURCE |
|---|---|
| S1 | Mercury lamp, LEITZ WETZLER Type 307-148.002, 100 W |
| S2 | Black Ray longwave UV lamp, model B-100A W/FLOOD |
| S3 | MELLES GRIOT He—Ne laser, 10 mW output, 1 = 632 nm |
| S4 | American laser corporation, argon ion laser, model 909BP-15-01001; 1 = 488 and 514 nm |

Numerous other dyes can be used for photopolymerization. These dyes include but are not limited to Erythrosin, phloxime, rose bengal, thionine, camphorquinone, ethyl eosin, eosin, methylene blue, and riboflavin. Possible cocatalysts that can be used include but are not limited to: N-methyl diethanolamine, N,N-dimethyl benzylamine, triethanolamine, triethylamine, dibenzyl amine, N-benzyl ethanolamine, N-isopropyl benzylamine.

EXAMPLE 32

Formation of Alginate-PLL-Alginate Microcapsules with Photopolymerizable Polycations Alginate-polylysine-alginate microcapsules were made by adsorbing, or coacervating, a polycation, such as polylysine (PLL), upon a gelled microsphere of alginate. The resulting membrane was held together by charge-charge interactions and thus has limited stability. To increase this stability, the polycation can be made photopolymerizable by the addition of carbon-carbon double bonds, for example. This can be used to increase the stability of the membrane by itself, or to react, for example, with photopolymerizable PEG to enhance biocompatibility.

To illustrate the synthesis of such a photopolymerizable polycation, 1 g of polyallylamine hydrochloride was weighed in 100 mL glass beaker and dissolved in 10 mL distilled water (DW). The pH of the polymer solution was adjusted to 7 using 0.2M sodium hydroxide solution. The polymer was then separated by precipitating in a large excess of acetone. It was then redissolved in 10 mL DW and the solution was transferred to 50 mL round bottom flask. Glycidyl methacrylate (0.2 mL) was slowly introduced into the reaction flask and the reaction mixture was stirred for 48 hours at room temperature. The solution was poured into 200 mL acetone and the precipitate was separated by filtration and dried in vacuum.

In addition to use in encapsulating cells in materials such as alginate, such photopolymerizable polycations may be useful as a primer or coupling agent to increase polymer adhesion to cells, cell aggregates, tissues, and synthetic materials, by virtue of adsorption of the photopolymerizable polymer bonding to the PEG photopolymerizable gel.

REFERENCES

Abuchowski, A. et al. (1977) J. Biol. Chem., 252:3578.
Amudeswari, S., et al. (1986) J. Biomed. Mater. Res. 20:1103–1109.
Andrade, J. D. et al. (1986) v. Adv. Polym. Sci., 79:1–63.
Baler, R. E. (1990) Biomaterials Forum, 12:20.
Buck, C. A. et al. (1987) Ann. Rev. Cell Biol., 3:179–205.
Chesneau, E. et al. (1985) Die Ange. Makromol. Chemie, 135:41, (1988) Makromol. Chem., Rapid Commun., 9:223; (1991) Makromol. Chem., 192:245
Chun, Y. Y. et al. (1981) "Studies on Microbial Transformations XIX. Use of Immobilized Cells of Streptomyces roseochromogenes for the 2 16 a-Hydroxylation of Dehydroepiandrosterone." J. Gen. App. Microbiol., 27:505–509.
Coleman, D. L., et al. (1982) J. Biomed. Mater. Res., 16:381–398.
Darquy, S. and Reach, G. (1985) Diabetologia, 28:776—780.
Dennison, K. A. (1986) Ph.D. Thesis. Massachusetts Institute of Technology.
Desai, N. P. et al. (1989) J. Biomaterials Sci., Polym. Ed., 1:123–146.
Desai, N. P. et al. (1989) Polym. Materials Sci. Eng., 62:731.
Desai, N. P. et al. (1991) Biomaterials, 12:144.
Desai, et al. (1992) Macromolecules 25:226.
Desai, N. P., et al. Biomaterials., in press.
Dupuy, B., et al. (1988) J. Biomed. Mater. Res., 22:1061–1070.
Eaton, D. F. (1986) Advances in Photochemistry, 13:427.
Fouassier, J. P. et al. (1985) J. Polym. Sci., Polym. Chem. Ed., 23:569.
Fouassier, J. P. et al. (1991) Makromol. Chem., 192:245–260.
Fukui, S. et al., (1976) "Application of Photo-Crosslinkable Resin to Immobilization of an Enzyme", Febs Letters, 66:2.
Fukui, S. et al., (1984) "Application of Biocatalysts Immobilized by Prepolymer Methods", Advances in Biochemical Engineering and Biotechnology, 29:1–33.
Gin, H., et al. (1987) J. Microencapsulation, 4:239–242.
Gombotz, W. R., et al. (1989) J. Appl. Poly. Sci., 37:91.
Goosen, M. F. A., et al. (1985) Biotechnology and Bioengineering, 27:146.
Harris, J. M. (1985) JNS-Rev. Macromol. Chem. Phys., C25:325–373.
Horbett, T. A. (1984) Thromb. Haemostas., 51:174.
Hoyle, C. E., et al. (1989) Macromolecules, 22:3866.
Hattori, S. et al. (1985) J. Col. Interface Sci., 104:72–78.
Hunt, C. A. et al., (1985) "Synthesis and Evaluation of a Prototypal Artificial Red Cell" Science, 6:1165–1168.
Iwata, H., et al. (1989) Diabetes, 38:224–225.

Karel, S. F., et al. (1985) Chem. and Engg. Science, 40(8):1321.

Karu, T. I. (1990) Photochem. and Photobiology, 52(6) 1089.

Kimura, A. et al. (1981), "Some properties of immobilized glycolysis system of yeast in fermentative phosphorylation of nucleotides," Eur. J. Appl Microbio. Biotechnol., 11:78–80.

Knowles, P. R., et al. (1990) Makromol. Chem., Macromol. Symp., 40:203–208.

Lambert, F. V., et al. (1984) Appl. Biochem. Biotech, 10:101–105.

McMahon, J., et al. (1990) J. Nat. Cancer Inst., 82(22) 1761–1765.

Miyama, H., et al. (1988) J. Appl. Polym. Sci., 35:115–125.

Nagoaka, S., et al. Polymers as Biomaterials, Shalaby, S. W. ed., Plenum Press, New York.

Neckers D.C., et al. (1989) Polym. Materials Sci. Eng., 60:15.

Okata, T. et al., (1987), "Application of entrapped growing yeast cells to peptide secretion system," Appl. Microbiol. Biotechnol., 26:112–116.

Omata, T., et al. (1979) "Immobilization of Microbial Cells and Enzymes with Hydrophobic Photo-Crosslinkable Resin Prepolymers" European J. Appl. Microbiol. Biotechnol., 6:207–215.

Omata, T., et al. (1979) "Transformation of Steroids by Gel-Entrapped *Nacardia rhodocrous* Cells in Organic Solvent" Eur. J. Appl. Microhiol. Biotechnol. 8:143–155.

Omata, T. et al. (1981), "Steroselectic hydrolysis of dimethyl succinate by gel-entrapped *Rhodotorula minuta* uzr. texensis cells in organic solvent," Eur. J. Appl. Microbial Biotechnol., 11:199–204.

O'Shea, G. M. et al. (1986) Diabetes, 35:943–946.

Park, T. G. et al. (1989) Biotechnology Letters, 11(1):17, For general references see c) Immobilized cells: Principles & and applications, J. Tampion and M. O. Tampion. Cambridge Univ. Press, (1987).

Rempp, P., et al. (1990) Polym. Prepr. (Am. Chem. Soc., Div. Polym. Chem.), 31:215.

Reuveny, S., et al. (1983) Biotechnol. Bioeng., 25:469–480.

Ronel, S. H. et al. U.S. Pat. No. 4,298,002, issued Nov. 3, 1981.

Sawhney, A. S. et al. "Biocompatible Microcapsules", U.S. patent application.

Seton, M. V, et al. (1987) J. Controlled Release, 6:177–187.

Sun, Y., et al. (1987) Polymer Prepr., 28:292–294.

Tanaka, A. et al., (1977), "Immobilization of Yeast Microbodies by Inclusion with Photo-cross linkable Resins" Eur J Biochem, 80: 193–197.

van Wachem, P. B., et al. (1987) Biomaterials, 8:323–328.

Wong et al. (1988) Biomat. Art. Cells, Art. Org., 16 (4) 731.

Wu, D. S. (November 1990) Laser Focus World, 99–106.

We claim:

1. A method for encapsulation of biological material comprising the steps of a) mixing the biological material in an aqueous macromer solution comprising macromer and photoinitiator, said biological material selected from the group consisting of tissue, cells, subcellular organelles and subcellular non-organelle components, said macromer comprising a water soluble polymer having at least two sites of unsaturation;

b) forming small geometric shapes of the mix in (a); and c) polymerizing the macromer by exposing the geometric shapes to light radiation.

2. The method of claim 1 wherein the biological material is first encapsulated in a microcapsule.

3. The method of claim 1 wherein the macromer is selected from the group consisting of ethylenically unsaturated derivatives of poly(ethylene oxide) (PEO), poly(ethylene glycol) (PEG), poly(vinyl alcohol) (PVA), poly(vinylpyrrolidone) (PVP), poly(ethyloxazoline) (PEOX), poly(amino acids), polysaccharides, and proteins.

4. The method of claim 3 wherein the PEG is PEG multiacrylate.

5. The method of claim 4 wherein the PEG is PEG tetraacrylate which has a molecular weight around 18,500 D.

6. The method of claim 3 wherein the polysaccharides are selected from the group consisting of alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives and carrageenan.

7. The method of claim 3 wherein the proteins are selected from the group consisting of gelatin, collagen and albumin.

8. The method of claim 1 wherein the macromer is of the formula

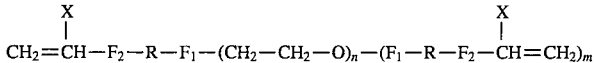

where $F_1$=CONH, COO or NHCOO

X=H, $CH_3$, $C_2H_5$, $C_6H_5$, Cl, Br, OH or $CH_2COOH$ $F_2$=COO, CONH, O or $C_6H_4$,

R=$CH_2$ or -alkyl-, $n \geq 5$, and $m \geq 2$.

9. The method of claim 1 wherein the photoinitiator is any dye which absorbs light having frequency between 320 nm and 900 nm, can form free radicals, is at least partially water soluble, and is non-toxic to the biological material at the concentration used for polymerization.

10. The method of claim 9 wherein the photoinitiator is selected from the group consisting of 2,2-dimethoxy,2-phenylacetophenone and 2-methoxy, 2-phenylacetophenone.

11. The method of claim 1 wherein the macromer solution further comprises a cocatalyst and the photoinitiator is selected from the group consisting of ethyl eosin, eosin Y, fluorescein, 2,2-dimethoxy,2-phenylacetophenone,2-methoxy,2-phenylacetophenone, camphorquinone, rose bengal, methylene blue, erythrosin, phloxime, thionine, riboflavin and methylene green.

12. The method of claim 11 wherein the cocatalyst is a nitrogen based compound capable of stimulating a free radical reaction.

13. The method of claim 11 wherein the cocatalyst is a a nitrogen atom-containing electron-rich molecule.

14. The method of claim 11 wherein the cocatalyst is a primary, secondary, tertiary or quaternary amine.

15. The method of claim 14 wherein the cocatalyst is selected from the group consisting of triethanolamine, triethylamine, ethanolamine, N-methyl diethanolamine, N,N-dimethyl benzylamine, dibenzyl amine, N-benzyl ethanolamine, N-isopropyl benzylamine, tetramethyl ethylenediamine, potassium persulfate, tetramethyl ethylenediamine, lysine, ornithine, histidine and arginine.

16. The method of claim 1 wherein the radiation has a wavelength between 320 nm and 900 nm.

17. The method of claim 16 wherein the radiation has a wavelength between 350 nm and 700 nm.

18. The method of claim 2 wherein the microcapsule is comprised of ionically coagulatable or thermally coagulatable polymers which are non-toxic to the encapsulated material.

19. The method of claim 1 wherein the cells are primary cells or established cell lines.

20. The method of claim 1 wherein the biological material is selected from pancreatic islet cells, human foreskin fibroblasts, Chinese hamster ovary cells, beta cell insulomas, lymphoblastic leukemia cells, mouse 3T3 fibroblasts, dopamine secreting ventral mesencephalon cells, neuroblastoid cells, adrenal medulla cells, and T-cells.

21. The method of claim 18 wherein the microcapsule is comprised of alginate.

22. The method of claim 18 wherein the microcapsule is comprised of chitosan.

23. The method of claim 18 wherein the microcapsule is comprised of agarose.

24. The method of claim 18 wherein the microcapsule is comprised of gelatin.

25. The method of claim 1 wherein the geometric shapes are formed by coextrusion of the aqueous macromer solution mixed with the biological material with a non-toxic, non-immunogenic, non-miscible substance capable of maintaining droplet formation.

26. The method of claim 25 wherein the non-miscible substance is oil.

27. The method of claim 26 wherein the oil is mineral oil.

28. The method of claim 1 wherein the geometric shapes are formed by coextrusion of the aqueous macromer solution mixed with the biological material in air.

29. The method of claim 1 wherein the geometric shapes are formed by agitation of the aqueous macromer solution mixed with the biological material with a non-toxic, non-immunogenic, non-miscible substance.

30. The method of claim 29 wherein the non-miscible substance is oil.

31. The method of claim 1 wherein the macromer solution further comprises an accelerator to accelerate the rate of polymerization.

32. The method of claim 31 wherein the accelerator is a small molecule containing an allyl, vinyl or acrylate group.

33. The method of claim 32 wherein the accelerator is selected from the group consisting of N-vinyl pyrolidinone, 2-vinyl pyridine, 1-vinyl imidazole, 9-vinyl carbazole, acrylic acid and 2-allyl,2-methyl,1-3-cyclopentane dione.

34. The method of claim 33 wherein the accelerator is N-vinyl pyrolidinone.

35. A method for encapsulation of biological material comprising the steps of
a) coating the biological material with photoinitiator, said biological material selected from the group consisting of tissue, cells, subcellular organelles, and subcellular non-organelle components;
b) suspending the coated material in an aqueous macromer solution, said macromer comprising a water soluble polymer having at least two sites of unsaturation; and
c) irradiating the suspension with light.

36. The method of claim 35 wherein the macromer is selected from the group consisting of ethylenically unsaturated derivatives of poly(ethylene oxide) (PEO), poly(ethylene glycol) (PEG), poly(vinyl alcohol) (PVA), poly(vinylpyrrolidone) (PVP), poly(ethyloxazoline) (PEOX), poly(amino acids), polysaccharides, and proteins.

37. The method of claim 36 wherein the PEG is PEG multiacrylate.

38. The method of claim 37 wherein the PEG is PEG tetraacrylate which has a molecular weight around 18,500 D.

39. The method of claim 36 wherein the polysaccharides are selected from the group consisting of alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives and carrageenan.

40. The method of claim 36 wherein the proteins are selected from the group consisting of gelatin, collagen and albumin.

41. The method of claim 35 wherein the macromer is of the formula $$CH_2=CH-F_2-R-F_1-(CH_2-CH_2-O)_n-(F_1-R-F_2-CH=CH_2)_m$$
$$\phantom{CH_2=CH-F_2-R-}{}^{|}_X \phantom{F_1-(CH_2-CH_2-O)_n-(F_1-R-F_2-CH=}{}^{|}_X$$

where $F_1$=CONH, COO or NHCOO

X=H, $CH_3$, $C_2H_5$, $C_6H_5$, Cl, Br, OH or $CH_2COOH$ $F_2$=COO, CONH, O or $C_6H_4$,

R=$CH_2$ or -alkyl-, $n \geq 5$, and $m \geq 2$.

42. The method of claim 35 wherein the photoinitiator is any dye which absorbs light having frequency between 320 nm and 900 nm, can form free radicals, is at least partially water soluble, and is non-toxic to the biological material at the concentration used for polymerization.

43. The method of claim 42 wherein the photoinitiator is selected from the group consisting of 2,2-dimethoxy,2-phenylacetophenone and 2-methoxy,2-phenylacetophenone.

44. The method of claim 35 wherein the macromer solution further comprises a cocatalyst and the photoinitiator is selected from the group consisting of ethyl eosin, eosin Y, fluorescein,2,2-dimethoxy,2-phenylacetophenone,2-methoxy,2-phenylacetophenone, camphorquinone, rose bengal, methylene blue, erythrosin, phloxime, thionine, riboflavin and methylene green.

45. The method of claim 44 wherein the cocatalyst is a nitrogen based compound capable of stimulating a free radical reaction.

46. The method of claim 44 wherein the cocatalyst is a a nitrogen atom-containing electron-rich molecule.

47. The method of claim 44 wherein the cocatalyst is a primary, secondary, tertiary or quaternary amine.

48. The method of claim 47 wherein the cocatalyst is selected from the group consisting of triethanolamine, triethylamine, ethanolamine, N-methyl diethanolamine, N,N-dimethyl benzylamine, dibenzyl amine, N-benzyl ethanolamine, N-isopropyl benzylamine, tetramethyl ethylenediamine, potassium persulfate, tetramethyl ethylenediamine, lysine, ornithine, histidine and arginine.

49. The method of claim 35 wherein the radiation has a wavelength between 320 nm and 900 nm.

50. The method of claim 49 wherein the radiation has a wavelength between 350 nm and 700 nm.

51. The method of claim 35 wherein the cells are primary cells or established cell lines.

52. The method of claim 35 wherein the biological material is selected from pancreatic islet cells, human foreskin fibroblasts, Chinese hamster ovary cells, beta cell insulomas, lymphoblastic leukemia cells, mouse 3T3 fibroblasts, dopamine secreting ventral mesencephalon cells, neuroblastoid cells, adrenal medulla cells, and T-cells.

53. The method of claim 35 wherein the geometric shapes are formed by coextrusion of the aqueous macromer solution mixed with the biological material with a non-toxic, non-immunogenic, non-miscible substance capable of maintaining droplet formation.

54. The method of claim 53 wherein the non-miscible substance is oil.

55. The method of claim 54 wherein the oil is mineral oil.

56. The method of claim 35 wherein the geometric shapes are formed by coextrusion of the aqueous macromer solution mixed with the biological material in air.

57. The method of claim 35 wherein the geometric shapes are formed by agitation of the aqueous macromer solution mixed with the biological material with a non-toxic, non-immunogenic, non-miscible substance.

58. The method of claim 57 wherein the non-miscible substance is oil.

59. The method of claim 35 wherein the biological material is first encapsulated in a microcapsule.

60. The method of claim 59 wherein the microcapsule is comprised of ionically coagulatable or thermally coagulatable polymers which are non-toxic to the encapsulated material.

61. The method of claim 60 wherein the microcapsule is comprised of alginate.

62. The method of claim 60 wherein the microcapsule is comprised of chitosan.

63. The method of claim 60 wherein the microcapsule is comprised of agarose.

64. The method of claim 60 wherein the microcapsule is comprised of gelatin.

65. The method of claim 35 wherein the macromer solution further comprises an accelerator to accelerate the rate of polymerization.

66. The method of claim 65 wherein the accelerator is a small molecule containing an allyl, vinyl or acrylate group.

67. The method of claim 66 wherein the accelerator is selected from the group consisting of N-vinyl pyrolidinone, 2-vinyl pyridine, 1-vinyl imidazole, 9-vinyl carbazole, acrylic acid and 2-allyl,2-methyl,1-3-cyclopentane dione.

68. The method of claim 67 wherein the accelerator is N-vinyl pyrolidinone.

69. The method of claim 31 wherein the macromer is poly(ethylene glycol) (PEG), the biological material is mammalian cells, and the accelerator is N-vinyl pyrrolidinone.

* * * * *

UNITED STATES PATENT AND TRADEMARK OFFICE
CERTIFICATE OF CORRECTION

PATENT NO. : 5,529,914
DATED : June 25, 1996
INVENTOR(S) : Jeffrey A. Hubbell

It is certified that error appears in the above-identified patent and that said Letters Patent is hereby corrected as shown below:

Column 7, line 7, delete "diacrylate,s" and insert — diacrylates —.

Column 15, line 2, delete "ClBr," and insert — Cl, Br, —.
Column 17, line 24, delete uz,13/32 Insulin/Islet/hr (µU/mL)*
   and insert — Insulin/Islet/hr (µU/mL)* —.
Column 25, line 65, delete "wets" and insert — was —.
Column 26, line 37, delete "Example 2" and insert — Example 21 —.
Column 26, line 42, delete "PEG—tetraacrylate" and insert
   — PEG tetraacrylate —.
Column 28, line 25, delete "agohist" and insert — agonist —.
Column 29, line 32, delete "of part" and insert — of 1 part —.
Column 29, line 37, delete "form gel" and insert — form a gel —.
Column 31, line 2, delete "application is" and insert —applications —.
Column 34, line 21, delete "Baler" and insert — Baier —.

Signed and Sealed this

Nineteenth Day of November, 1996

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,529,914
DATED : June 25, 1996
INVENTOR(S) : Jeffrey A. Hubbell, et al It is certified that error appears in the above-identified patent and that said Letters Patent is hereby corrected as shown below:

Column 4, line 15, delete "et" and insert -- et al. --.
Column 4, line 25, delete "he" and insert -- the --.
Column 7, line 7, delete "diacrylate,s" and insert -- diacrylates --.
Column 10, line 66, delete "4,391909" and insert -- 4,391,909 --.
Column 15, line 2, delete "ClBr," and insert -- Cl, Br, --.
Column 17, line 24, delete uz,13/32 Insulin/Islet/hr (µU/mL)*
    and insert -- Insulin/Islet/hr (µU/mL)* --.
Column 25, line 65, delete "wets" and insert -- was --.
Column 26, line 37, delete "Example 2" and insert -- Example 21 --.
Column 26, line 42, delete "PEG--tetraacrylate" and insert
    -- PEG tetraacrylate --.
Column 28, line 25, delete "agohist" and insert -- agonist --.
Column 29, line 32, delete "of part" and insert -- of 1 part --.
Column 29, line 37, delete "form gel" and insert -- form a gel --.
Column 31, line 2, delete "application is" and insert --applications --.
Column 34, line 21, delete "Baler" and insert -- Baier --.

UNITED STATES PATENT AND TRADEMARK OFFICE
CERTIFICATE OF CORRECTION

PATENT NO. : 5,529,914
DATED : June 25, 1996
INVENTOR(S) : Jeffrey A. Hubbell, et al It is certified that error appears in the above-identified patent and that said Letters Patent is hereby corrected as shown below:

Column 34, line 66, delete "Red Cell" Science and insert -- Red Cell", Science --.

Column 35, line 52, delete "Seton, M.V. et al." and insert -- Sefton, M.V. et al. --.

Column 40, please add the following claim:

70. The method of claim 1 wherein the geometric shape is selected from the group consisting of cylinders, slabs, discoidal shapes, globular shapes and spheres.

Sheet 2 of 12, Fig. 2a, delete "MOMONER" and insert -- MONOMER --.
Sheet 2 of 12, Fig. 3, delete "IRRADIATED WITH LAZER" and insert -- IRRADIATED WITH LASER --.

This certificate supersedes Certificate of Correction issued November 19, 1996.

Signed and Sealed this

Seventeenth Day of November, 1998

*Attest:*

BRUCE LEHMAN

*Attesting Officer*    Commissioner of Patents and Trademarks